(12) United States Patent
Zhang et al.

(10) Patent No.: US 10,988,481 B2
(45) Date of Patent: Apr. 27, 2021

(54) POTENT AND SELECTIVE MU OPIOID RECEPTOR MODULATORS

(71) Applicant: VIRGINIA COMMONWEALTH UNIVERSITY, Richmond, VA (US)

(72) Inventors: Yan Zhang, Richmond, VA (US); Dana E. Selley, Richmond, VA (US); William Dewey, Richmond, VA (US); Hamid Abkarali, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/301,765

(22) PCT Filed: May 16, 2017

(86) PCT No.: PCT/US2017/032792
§ 371 (c)(1),
(2) Date: Nov. 15, 2018

(87) PCT Pub. No.: WO2017/200970
PCT Pub. Date: Nov. 23, 2017

(65) Prior Publication Data
US 2019/0152982 A1    May 23, 2019

Related U.S. Application Data

(60) Provisional application No. 62/338,636, filed on May 19, 2016.

(51) Int. Cl.
*A61P 25/30* (2006.01)
*C07D 489/08* (2006.01)
*A61P 25/04* (2006.01)

(52) U.S. Cl.
CPC ............ *C07D 489/08* (2013.01); *A61P 25/04* (2018.01); *A61P 25/30* (2018.01)

(58) Field of Classification Search
CPC .............................. A61P 25/30; C07D 489/08
IPC .............................. A61P 25/30; C07D 489/08
See application file for complete search history.

(56) References Cited

U.S. PATENT DOCUMENTS

| | | | |
|---|---|---|---|
| 5,330,986 A | 7/1994 | Shutske | |
| 6,323,212 B1 * | 11/2001 | Nagase | C07D 409/12 514/282 |
| 7,320,984 B2 | 1/2008 | Isumimoto et al. | |
| 8,772,308 B2 * | 7/2014 | Zhang | A61P 25/32 514/282 |
| 2013/0224151 A1 | 8/2013 | Pearson et al. | |
| 2013/0281698 A1 | 10/2013 | Schuetz et al. | |
| 2014/0371255 A1 | 12/2014 | Zhang et al. | |
| 2015/0203504 A1 | 7/2015 | Goehring et al. | |

FOREIGN PATENT DOCUMENTS

WO    2012/166891 A2    12/2012

OTHER PUBLICATIONS

Lindsey, G.L., et al. "Design, Synthesis, and Biological Evaluation of 6α- and 6β-N-Heterocyclic Substituted Naltrexamine Derivatives as μ Opioid Receptor Selective Antagonists." J. Med. Chem. (2009), vol. 52, pp. 1416-1427. (Year: 2009).*

* cited by examiner

Primary Examiner — John S Kenyon
(74) Attorney, Agent, or Firm — W&C IP

(57) ABSTRACT

Analogues of 6 α/β-naltrexamine (NAQ) are provided. The analogues are selective, reversible antagonists of the mu opioid receptor (MOR) that exhibit good blood brain barrier penetration. The compounds are used in the treatment of opioid addiction and other diseases and conditions, including for the treatment of pain.

3 Claims, 3 Drawing Sheets

POTENT AND SELECTIVE MU OPIOID RECEPTOR MODULATORS

CROSS-REFERENCE TO RELATED APPLICATIONS

This application claims benefit of U.S. provisional patent application 62/388,636, filed May 19, 2016, the complete contents of which is hereby incorporated by reference.

STATEMENT OF FEDERALLY SPONSORED RESEARCH AND DEVELOPMENT

This invention was made with government support under grant number DA024022 awarded by the National Institutes of Health/National Institutes on Drug Abuse. The United States government has certain rights in the invention.

BACKGROUND OF THE INVENTION

Field of the Invention

The invention generally relates to Mu opioid receptor (MOR) modulators and methods of their use. In particular, the invention provides potent non-peptidyl selective and reversible MOR antagonists that are naltrexamine analogues, and methods of using them to treat opioid addiction, pain and other conditions.

Background

It is estimated that between 26.4 million and 36 million people abuse opioids such as heroin, morphine, and other prescription pain relievers worldwide, and this abuse affects the health, social, and economic welfare of every demographic group. An alarming observation is that opioid misuse is on the rise. For example, the number of unintentional overdose deaths from opioid prescription analgesics has soared in the United States, more than quadrupling since 1999. Therefore, opioid addiction has become a global epidemic and has affected the economies of many countries. Effective drug addiction treatment has been shown to reduce associated health and social cost far more than the cost of treatment itself. Therefore, treating opioid addicts rather than imprisoning them would drive down the huge cost associated with substance abuse.

Opioid antagonists such as naltrexone and naloxone target opioid receptors and have been shown to curb drug craving and prevent relapse. However, severe side effects (e.g. depression, dysphoria, pulmonary edema and cardiac arrhythmias) have been reported when these drugs are used as long-term treatments for opioid addiction. The side effects are likely due to the lack of selectivity for the Mu opioid receptor (MOR) over other opioid receptors, namely the delta-opioid receptor (DOR) and the kappa-opioid receptor (KOR). For example, DOR activation has antidepressant and anxiolytic effects and also plays an important role in neuroprotection and cell proliferation, and KOR agonists and partial agonists have been shown to produce psychotomimetic and dysphoric effects. Therefore, an ideal agent to treat opioid addiction without the severe side effects would be a highly selective MOR antagonist.

Some selective MOR antagonist such as β-FNA and clocinnamox have been developed, but these agents bind irreversibly to MOR, which limits their use as drugs. Cyprodime is a reversible MOR antagonist that has been intensively studied. However, it has a lower affinity for MOR than naltrexone and naloxone and it has only moderate selectivity for MOR (KOR/MOR≈10, DOR/MOR≈39). The highly selective MOR antagonists that have been identified are conformationally constrained peptides such as D-Phe-Cys-Tyr-D-Trp-Orn-Thr-Pen-Thr-NH$_2$ (CTOP; SEQ ID NO: 1) and D-Phe-Cys-Tyr-D-Trp-Arg-Thr-Pen-Thr-NH$_2$ (CTAP; SEQ ID NO: 2). However, CTOP and CTAP have limited bioavailability and have poor blood-brain barrier penetration capacity, making them unsuitable as drug development candidates.

There is thus a pressing need to develop new opioid addiction treatment medications with fewer side effects. In particular, it would be beneficial to have available potent, highly selective, and reversible antagonists for MOR that exhibit high bioavailability and good blood-brain barrier penetration capacity.

SUMMARY OF THE INVENTION

Other features and advantages of the present invention are set forth in the description of invention that follows, and in part will be apparent from the description or may be learned by practice of the invention. The invention is realized and attained by the compositions and methods particularly pointed out in the written description and claims.

Provided herein are novel non-peptidyl, selective, and reversible MOR antagonists with high blood-brain barrier penetration capacity. Based on homology modeling studies of the three opioid receptor types and binding mode analyses of naltrexone in these models, two exemplary series of novel 6 α/β-naltrexamine (NAQ) analogues were designed, synthesized and analyzed. The results of in vitro competition binding assays and in vivo functional studies show that the compounds are potent, selective and reversible MOR antagonists. Significantly, the compounds have less efficacy at DOR than NAQ but they retain NAQ's low efficacy at KOR and high selectivity for MOR. The compounds thus have high therapeutic value in treating opioid addiction.

It is an object of this invention to provide compound with generic Formula I:

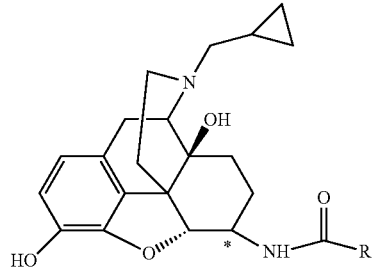

Formula I wherein * indicates a chiral C that can be either an R configuration or an S configuration in terms of chirality; and R of Formula I=

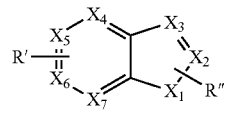

and is bonded to Formula I at $X_2$, $X_3$, $X_4$, $X_5$, $X_6$ or $X_7$; and wherein: $X_1$=N, O or S; one or more of $X_4$, $X_5$, $X_6$ and $X_7$ are independently substituted by R' where R'=a straight chain or branched alkyl group, a straight chain or branched alkene group, an electron withdrawing group, or an electron donating group, and one or both of $X_2$ and $X_3$ are independently substituted by R" where R"=a straight chain or branched alkyl group, a straight chain or branched alkene group, an electron withdrawing group, or an electron donating group; and salts thereof; with the caveat that R is not:

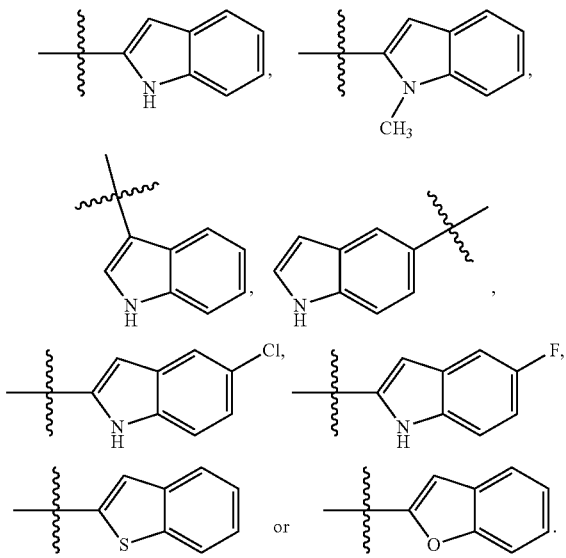

In some aspects, the straight chain or branched alkyl group comprises from about 1 to about 20 carbon atoms. In other aspects, the straight chain or branched alkyl group is selected from the group consisting of methyl, ethyl, propyl, isopropyl, butyl, pentyl, heptyl, septyl, octyl, nonyl, decyl, undecyl and dodecyl, and isomers (e.g. stereoisomers) thereof. In other aspects, the electron withdrawing group is selected from the group consisting of F, CN, $NO_2$, $SO_3$ and $CF_3$. In further aspects, the electron donating group is $OCH_3$, phenyl or substituted phenyl.

The invention also provides methods of treating opioid addiction in a subject in need thereof, comprising administering to the subject a therapeutically effective amount of a compound of Formula I:

Formula I

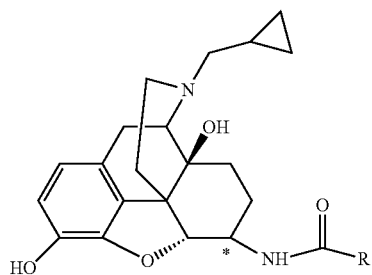

wherein * indicates a chiral C that can be either an R configuration or an S configuration in terms of chirality; and R of Formula I=

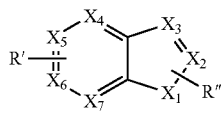

and is bonded to Formula I at $X_2$, $X_3$, $X_4$, $X_5$, $X_6$ or $X_7$; and wherein $X_1$=N, O or S; one or more of $X_4$, $X_5$, $X_6$ and $X_7$ are independently substituted by R' where R'=a straight chain or branched alkyl group, a straight chain or branched alkene group, an electron withdrawing group, or an electron donating group, and one or both of $X_2$ and $X_3$ are independently substituted by R" where R"=a straight chain or branched alkyl group, a straight chain or branched alkene group, an electron withdrawing group, or an electron donating group; or a physiologically acceptable salt thereof. In some aspects, the straight chain or branched alkyl group comprises from 1 to 20 carbon atoms. In other aspects, the straight chain or branched alkyl group is selected from the group consisting of methyl, ethyl, propyl, isopropyl, butyl, pentyl, heptyl, septyl, octyl, nonyl, decyl, undecyl and dodecyl, and isomers thereof. In further aspects, the electron withdrawing group is selected from the group consisting of F, CN, $NO_2$, $SO_3$ and $CF_3$. In additional aspects, the electron donating group is $OCH_3$, phenyl or substituted phenyl. In some aspects, the compound is

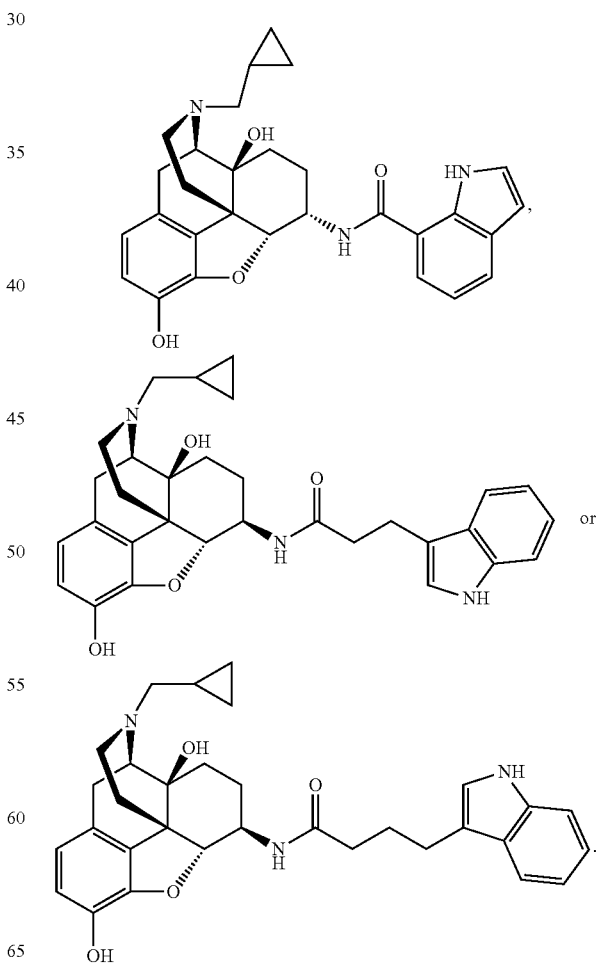

The invention further provides methods of treating pain in a subject in need thereof, comprising administering to the subject a therapeutically effective amount of a compound of Formula I:

Formula I

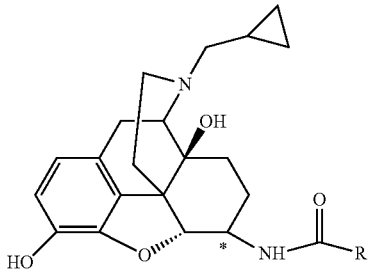

wherein * indicates a chiral C that can be either an R configuration or an S configuration in terms of chirality; and R of Formula I=

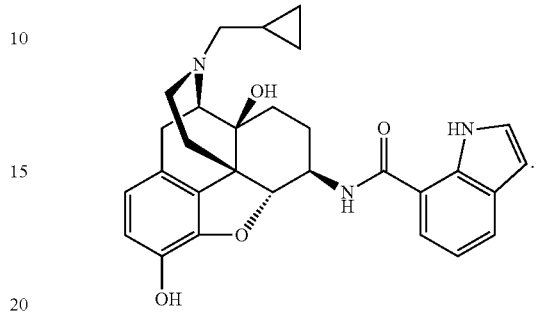

and is bonded to Formula I at $X_2$, $X_3$, $X_4$, $X_5$, $X_6$ or $X_7$; and wherein $X_1$=N, O or S; one or more of $X_4$, $X_5$, $X_6$ and $X_7$ are independently substituted by R' where R'=a straight chain or branched alkyl group, a straight chain or branched alkene group, an electron withdrawing group, or an electron donating group, and one or both of $X_2$ and $X_3$ are independently substituted by R" where R"=a straight chain or branched alkyl group, a straight chain or branched alkene group, an electron withdrawing group, or an electron donating group; or a physiologically acceptable salt thereof; with the caveat that R is not:

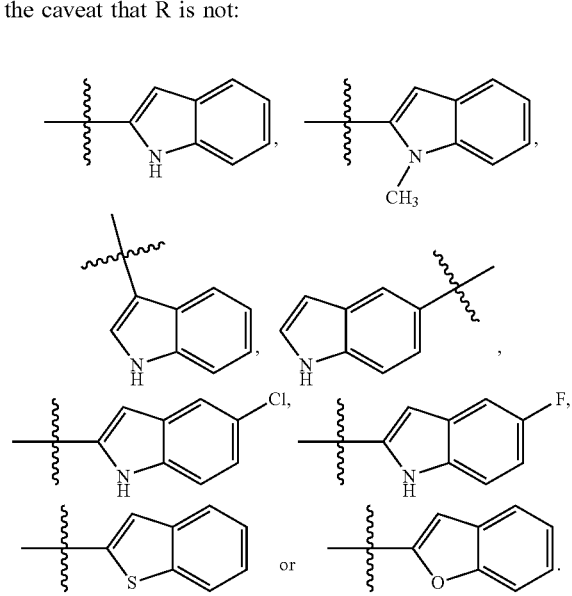

In some aspects, the straight chain or branched alkyl group comprises from 1 to 20 carbon atoms. In other aspects, the straight chain or branched alkyl group is selected from the group consisting of methyl, ethyl, propyl, isopropyl, butyl, pentyl, heptyl, septyl, octyl, nonyl, decyl, undecyl and dodecyl, and isomers thereof. In further aspects, the electron withdrawing group is selected from the group consisting of F, CN, $NO_2$, $SO_3$ and $CF_3$. In additional aspects, the electron donating group is $OCH_3$, phenyl or substituted phenyl. In some aspects, the compound is

DETAILED DESCRIPTION

Figure 1A:
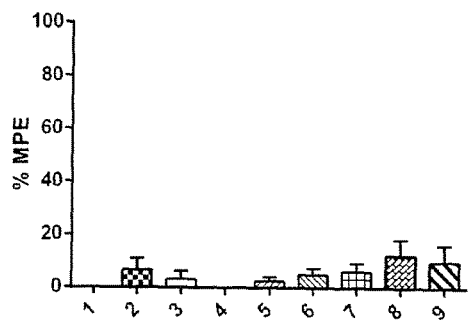
FIG. 1A-D. Warm-water tail immersion assay in mice (n=5) at 56±0.1° C. All tested compounds were administered subcutaneously (s.c.). Antinociceptive effects of (A) indole analogues of 6α-naltrexamine (B) indole analogues of 6β-naltrexamine. Compounds (10 mg/kg) were injected at Time 0. Twenty minutes after injection, tail flick was assessed with hot water. Blockage of the antinociceptive effect of morphine by (C) indole analogues of 6α-naltrexamine (D) indole analogues of 6β-naltrexamine. Tested compounds (10 mg/kg) were injected at Time 0. Five minutes later, morphine (10 mg/kg) was administered. Twenty minutes after morphine injection, tail flick was tested using hot water.

Described herein are non-peptidyl compounds that are potent MOR antagonists. The antagonists are highly selective and reversible, and thus in some aspects, the compounds are used to treat opioid addiction. In some aspects, certain of the compounds are also used to treat other conditions such as pain.

By "antagonist" we mean a substance that interferes with or inhibits the physiological action of another. In this case, the substance is one or more compounds as described herein, and the "another" is one or more of the MOR, the KOR and/or the DOR, especially the MOR.

As used herein "chiral center" or "stereocenter" refers to an atom in a compound at which the spatial arrangement of atoms or atomic groups bonded to the chiral atom is such that the compound is not superposable on its mirror image. Chiral centers are assigned a configuration of either R (rectus) or S (sinister) according to well defined Cahn—Ingold—Prelog rules.

The compounds disclosed herein have the general formula shown in Formula I:

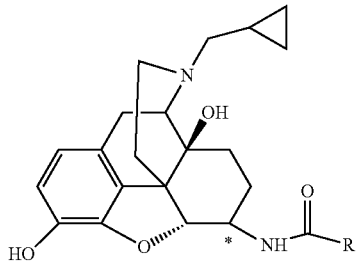

Formula I where * indicates a chiral C where the arrangement of atoms bonded to C can be either R or S, in terms of chirality; and where the R substituent (variable group or component) of Formula I (i.e. the R that is bonded to C of NHC=O ) is

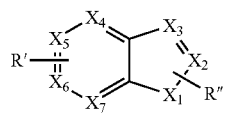

wherein:
the substituent R is bonded to Formula I at $X_2$, $X_3$, $X_4$, $X_5$, $X_6$ or $X_7$ of R;
$X_1$ of substituent R is nitrogen (N), oxygen (O) or sulfur (S);
one or more of $X_4$, $X_5$, $X_6$ and $X_7$ are independently substituted by R' where R'=a straight or branched, saturated or unsaturated carbon chain, an electron withdrawing group, or an electron donating group; and
one or more of $X_2$ and $X_3$ are independently substituted by R" where R"=a straight or branched, saturated or unsaturated carbon chain, an electron withdrawing group, or an electron donating group,
with the caveat that, in the compound of Formula I, R is not:

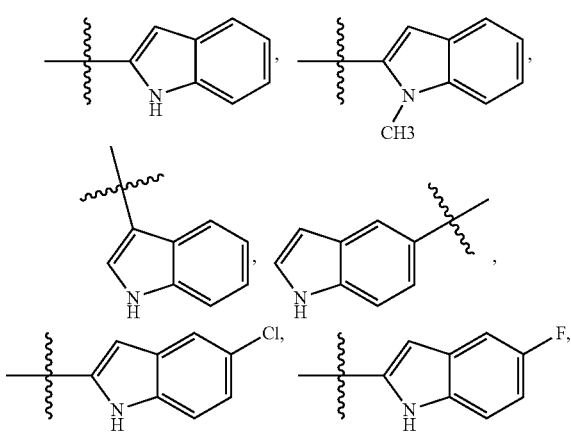

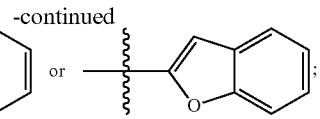

as well as salts thereof, which may be physiologically acceptable or compatible salts. However, this caveat does not apply for the use of the compounds of the invention to treat e.g. drug addiction such as opioid addiction.

Accordingly, the invention also provides methods of treating opioid addition by administering a therapeutically effective amount of at least one compound having the general formula shown in Formula I:

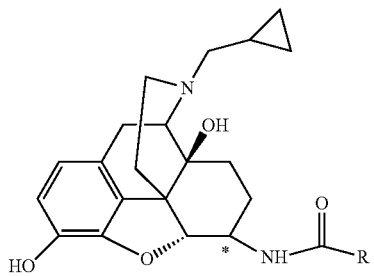

Formula I where * indicates a chiral C where the arrangement of atoms bonded to C can be either R or S, in terms of chirality; and where the R substituent (variable group or component) of Formula I (i.e. the R that is bonded to C of NHC=O ) is

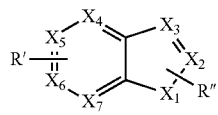

wherein:
the substituent R is bonded to Formula I at $X_2$, $X_3$, $X_4$, $X_5$, $X_6$ or $X_7$ of R;
$X_1$ of substituent R is nitrogen (N), oxygen (O) or sulfur (S);
one or more of $X_4$, $X_5$, $X_6$ and $X_7$ are independently substituted by R' where R'=a straight or branched, saturated or unsaturated carbon chain, an electron withdrawing group, or an electron donating group; and
one or more of $X_2$ and $X_3$ are independently substituted by R" where R"=a straight or branched, saturated or unsaturated carbon chain, an electron withdrawing group, or an electron donating group.

For both R' and R", suitable straight or branched, saturated or unsaturated carbon chains include but are not limited to those that contain from about 1 to about 20 carbon atoms. In some aspects, the carbon chain is saturated, i.e. the carbon chain is an alkyl chain. Examples of suitable alkyl groups include but are not limited to methyl, ethyl, propyl, isopropyl, butyl, pentyl, heptyl, septyl, octyl, nonyl, decyl, undecyl and dodecyl, as well as branched isomers thereof, and substituted variants thereof. Alternatively, the branched or unbranched carbon chain may be unsaturated alkenes, e.g. containing one or more (e.g. 1, 2, 3, 4, or 5 or more) double bonds. For example, suitable lower alkenes containing 1 double bond include but are not limited to e.g. ethane, propene, butene, etc.

For both R' and R", suitable electron withdrawing groups include but are not limited to, e.g. halogens such as F, CN, $NO_2$, $SO_3$, $CF_3$, $NR_2$, OR, NHCOR (where R is H or a lower alkyl with from about 1-5 carbon atoms such as methyl, ethyl, propyl, butyl, pentyl, etc., or an alkene equivalent).

For both R' and R", suitable electron donating groups include but are not limited to, e.g. alkyl groups; alkoxyl groups (e.g. OR where R=H or a lower alkyl); alcohol groups (methanol, ethanol, propanol, etc.); amino and substituted amino groups, etc. Exemplary functional groups include but are not limited to $OCH_3$, phenyl and substituted phenyl.

The compounds described herein generally have a binding affinity (Ki) for MOR in the range of from about 1.0 to about 0.05, and preferably in the range of from about 0.8 to about 0.1, e.g. about 0.8, 0.7, 0.6, 0.5, 0.4, 0.3, 0.2 or 0.1. Generally, the compounds have a Ki for the KOR in the range of from about 0.15 to about 4.0, or about 0.2 to about 3.0, or about 0.25 to about 2.0 or even about 0.3 to about 1.0, including all intervening integers and decimals to two decimal places. Further, the compounds generally have a Ki for the DOR in the range of from about 50 to about 0.5, e.g. about 40 to about 0.75, or about 30 to about 1.0, or even from about 20 to about 5.0, including all intervening integers and decimals to two decimal places. Typically, the ratio of KOR/MOR affinity ranges from about 15.0 to about 0.1, e.g. from about 12.0 to about 0.5, for example from about 5.0 to about 1.0, such as about 5.0, 4.0, 3.0, 2.0 or 1.0, including all intervening integers and decimals to two decimal places (5.0, 4.99, 4.98, etc.). Similarly, the DOR/MOR affinity ratio is generally in the range of from about 200 to about 5, e.g. about 100 to about 10, such as about 100, 90, 80, 70, 60, 50, 40, 30, 20 or 10, including all intervening integers and decimals to two decimal places.

The compounds described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations and compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, pharmaceutically acceptable salts and the like. In some aspects, various thickeners, flavorings, diluents, emulsifiers, dispersing aids or binders and the like are added. The compositions of the present invention may contain any such additional ingredients so as to provide the composition in a form suitable for administration. The final amount of compound in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compositions are administered in vivo by any suitable route including but not limited to: inoculation or injection (e.g. intravenous, intraperitoneal, intramuscular, subcutaneous, intra-aural, intra-ocular, intraarticular, intramammary, and the like); or by absorption through epithelial or mucocutaneous linings. Other suitable means include but are not limited to: inhalation (e.g. as a mist or spray) and orally (e.g. as a pill, capsule, liquid, etc.). In preferred embodiments, the mode of administration is oral. In addition, the compositions may be administered in conjunction with other treatment modalities.

The amount of a compound that is administered depends on several factors, e.g. the weight, gender, age, overall health, etc. of the recipient, and is best determined by a skilled medical practitioner such as a physician. However, the amount is generally in the range of from about 1-1000 mg/kg of body weight, e.g. from about 5-500 or about 10-250 or about 15-125 mg/kg of body weight, including all integers and fractional values within these ranges.

The compounds described herein generally are used to target diseases and conditions which can be prevented or treated by antagonizing the MOR. Exemplary conditions and symptoms thereof that are prevented and/or treated using the compounds described herein include but are not limited to: pain of any type, including neuropathic pain; substance abuse and addiction (e.g. opioid, cocaine, alcohol, amphetamine, methamphetamine, bath salts, etc.) in which case the present non-addictive compounds can be substituted for the addictive substance; Parkinson's disease; obesity; epilepsy; inflammation; gastrointestinal tract disorders such as constipation and irritable bowel syndrome (IBS); AIDs; various psychological disorders such as depression, schizophrenia, bipolar disorder, schizoaffective disorder, gambling addiction, etc.; and others. The addictions (dependencies) that may be treated include both recreational addictions which occur as the result of illegal substance abuse, and addictions that result from the legal administration of drugs under the care of a medical professional, e.g. to treat pain.

However, varying degrees of affinity for the KOR and the DOR are exhibited by the compounds, and some may be suitable for preventing or treating diseases and conditions which are treatable by antagonizing the KOR or the DOR (alone or on combination with the MOR), or the KOR and the DOR (alone or on combination with the MOR).

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Design, Synthesis and Pharmacological Characterization of Indole Analogues of 6 α/β-naltrexamine (NAQ)

Introduction

Naltrexamine (17-cyclopropylmethyl-3,14β-dihydroxy-4,5α-epoxy-6α (isoquinoline-3-carboxamido)morphinan or NAQ) is a MOR selective antagonist that acts in the central nervous system and has been shown to hold tremendous promise as a candidate or lead compound to treat opioid addiction (Schiff, P. L. Opium and Its Alkaloids. Am. J. Pharm. Educ. 2002, 66, 186-194; Katz, N. P. et al. Clin. J. Pain 2007, 23 (8), 648-660). However, NAQ's selectivity for MOR over DOR (146 fold) is lower than that of naltrexone (435 fold) (Meldrum, M. L. A Capsule History of Pain Management. JAMA 2003, 290 (18), 2470-2475). Even though NAQ has low efficacy at KOR, it has high efficacy and moderate potency at DOR. Studies have demonstrated that DOR activation is involved in the development of morphine dependence and also, deletion of the genes for DOR inhibits the development of morphine tolerance. Thus, new compounds having less efficacy at DOR in addition to retaining NAQ's low efficacy at KOR with high selectivity for MOR would have more therapeutic value in treating opioid addiction.

Through molecular modeling and mutagenesis studies, it was demonstrated that the selectivity of NAQ for MOR is as a result of its π-π stacking with W318 of MOR. To explore whether other heterocyclic ring systems might form π-π interactions with W318, new compounds were designed in which the isoquinoline ring of NAQ was replaced with an indole ring. It was theorized that introducing other heterocyclic ring systems might yield compounds with improved pharmacologic (increased selectivity and reduced partial agonist effect) and drug-like properties (improved absorption, distribution, metabolism, and excretion properties) and might lead to the identification of new lead compounds.

Materials and Methods

Synthesis

Naltrexone was used as the starting material in the synthesis of both 6α-naltrexamine (22) and 6β-naltrexamine (25). In the synthesis of 6α-naltrexamine HCl, (Scheme 1, route A) a reductive amination was conducted between naltrexone and benzyl amine. The Schiff base formed (22) was reduced and the benzyl group cleaved off using hydrogenation. However, dibenzyl amine was refluxed with naltrexone to synthesize 6β-naltrexamine HCl (Courtwright, D. T.; Joseph, H.; DesJarlais, D. Addicts Who Survived; University of Tennessee Press: Knoxville, Tenn., 1989). The reduction of Schiff base of benzyl naltrexamine yielded the 6α-isomer because the ring adopts a chair-like conformation. Therefore, hydride transfer occurs on the β-face leading to the formation of the 6α-isomer. On the other hand, the Schiff base of dibenzyl naltrexamine adopts a boat conformation. Therefore, hydride transfer from NaCNBH₃, occurs exclusively on the more accessible α face, thereby leading to the 6β isomer. Details of the syntheses and characterizations are given in Example 2 below.

Synthesis of Indole Analogues Substituted at 6 Position of Naltrexamine

6α/β naltrexamine HCl were coupled to their respective indole carboxylic acids using EDCI coupling (Scheme 2). This coupling reaction also results in the formation of an ester at position 3. The ester group was then hydrolyzed since esters are more susceptible to hydrolysis than amides. The final compounds synthesized were converted to the HCl salt and the percentage yield obtained for each compound is shown in Table 1. The percentage yield obtained for the 6α-naltrexamine derivatives ranged from 22-81% while that for the 6(3-naltrexamine derivatives ranged from 23-61%. Details of the syntheses and characterizations are given in Example 2 below.

Scheme 1. Synthesis of 6α/β naltrexamine HCl

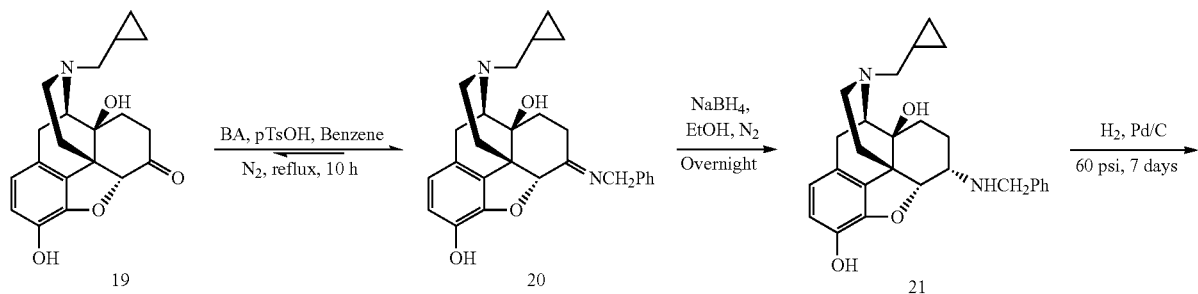

A

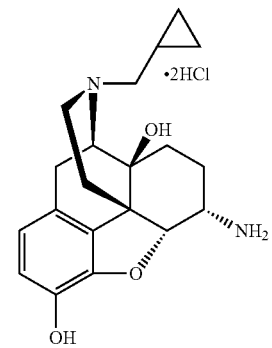

22

-continued
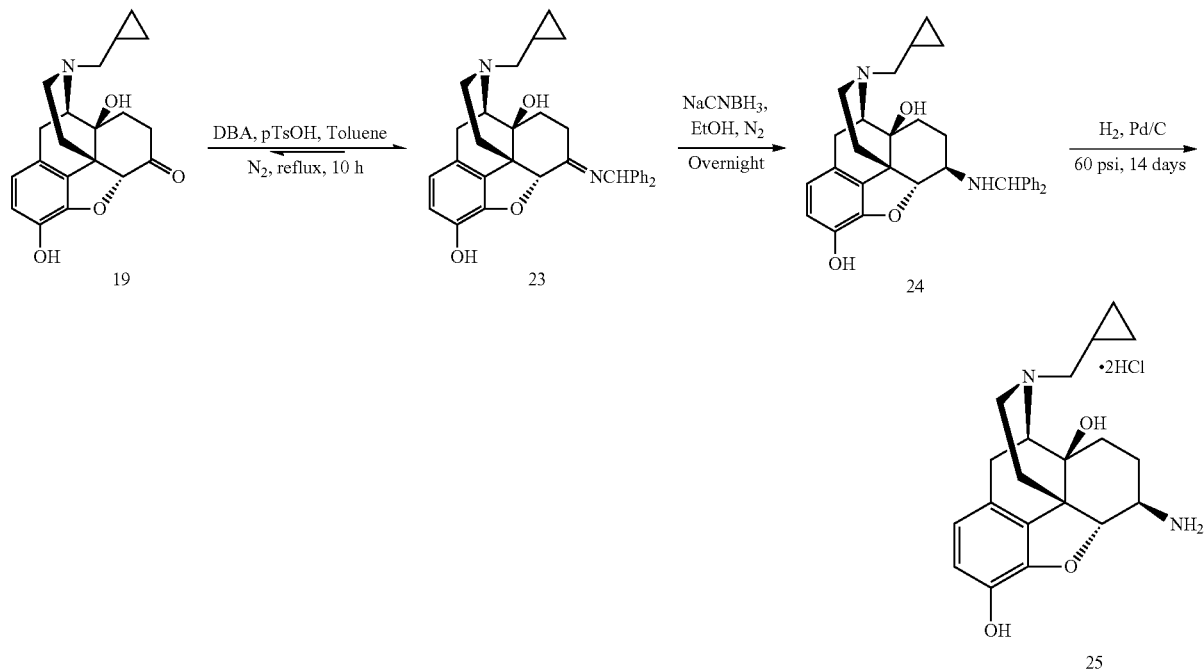
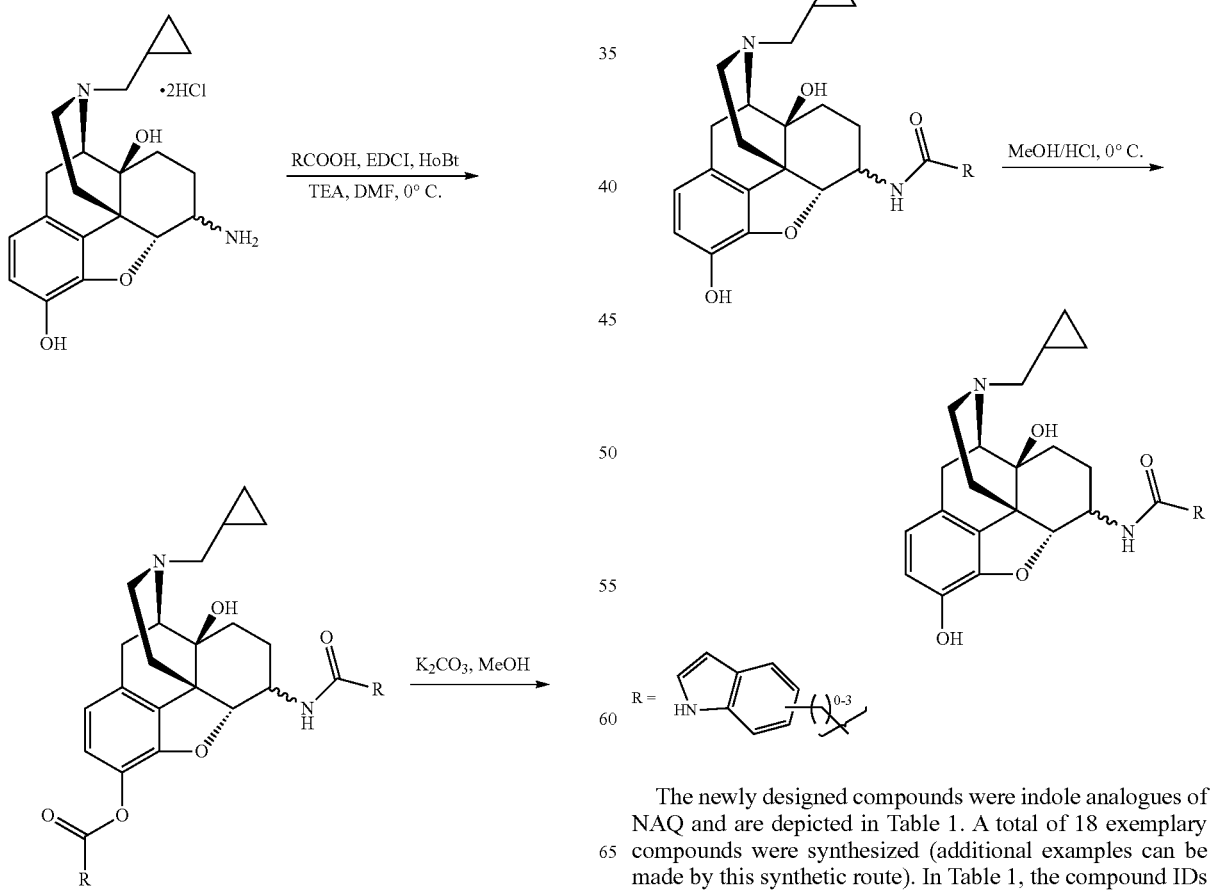
The newly designed compounds were indole analogues of NAQ and are depicted in Table 1. A total of 18 exemplary compounds were synthesized (additional examples can be made by this synthetic route). In Table 1, the compound IDs for the 6α-naltrexamine derivatives are in black while the compound IDs for the 6β-naltrexamine derivatives are in grey. Percentages are percent yields. The final compounds were characterized by ¹HNMR, ¹³CNMR, HRMS and IR and the purity determined by HPLC.

TABLE 1

Indole analogues of NAQ

6α-naltrexamine analogues

6β-naltrexamine analogues

| | | |
|---|---|---|
| 1 | | 81% |
| 10 | 2-indolyl | 32% |
| 2 | | 29% |
| 11 | 3-indolyl | 23% |
| 3 | | 80% |
| 12 | 4-indolyl | 31% |
| 4 | | 50% |
| 13 | 5-indolyl | 61% |

TABLE 1-continued

Indole analogues of NAQ

6α-naltrexamine analogues

6β-naltrexamine analogues

| | | |
|---|---|---|
| 5 | | 75% |
| 14 | 6-indolyl | 29% |
| 6 | | 22% |
| 15 | 7-indolyl | 56% |
| 7 | | 80% |
| 16 | indol-3-ylmethyl | 49% |
| 8 | | 55% |
| 17 | indol-3-ylethyl | 51% |

TABLE 1-continued

Indole analogues of NAQ

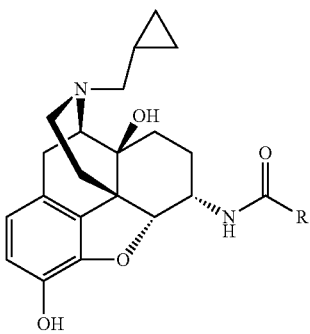

6α-naltrexamine
analogues

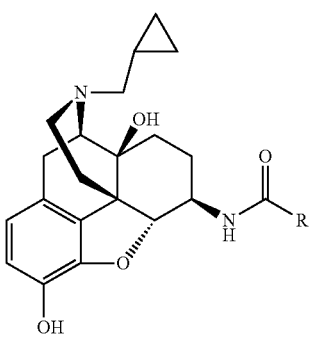

6β-naltrexamine
analogues

| 9 | 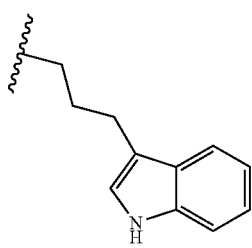 [SMILES: *CCCc1c[nH]c2ccccc12] | 34% |
| 18 | | 39% |

Pharmacological Characterization

Pharmacological assays were conducted to determine the binding affinity, selectivity and functional activity of the synthesized compounds.

Cell Culture

Chinese hamster ovary (CHO) cells expressing MOR, KOR and DOR were cultured for use in this assay. The culture media used for MOR CHO cells contained 500 mL DMEM/F12 media, 10% FBS, 1% penicillin/streptomycin, and 2.75 mL G418. The DOR and KOR CHO cells were cultured in the same media except that 5% FBS was used instead of 10%. The cells are allowed to grow until they are 80-95% confluent after which they are split. The cells are continuously cultured and split until there were sufficient cells for the studies.

Cell Membrane Harvesting

Once the cells reached confluence, cells were harvested, centrifuged at 1000×g for 10 minutes, and suspended in membrane buffer (50 mM Tris, 3 mM $MgCl_2$, and 1 mM EGTA, pH 7.4). The cells were then homogenized, centrifuged at 50000×g for 10 minutes, and re-homogenized in membrane buffer. A Bradford assay was conducted to determine membrane protein concentrations, and membrane protein preps (3 μg/aliquot) were stored at −80° C.

Competition Binding Assay

The competition binding assay was conducted to determine the affinity and selectivity of the synthesized compounds to MOR over KOR and DOR. The Kd and Bmax values for [$^3$H]NLX at MOR and [$^3$H]DPN at KOR had been determined previously. The Kd and Bmax values for [$^3$H] DPN at DOR were determined using varying concentrations of [$^3$H]DPN and fixed a concentration of 30 μg DOR membrane protein and 5 μM SNC80. [$^3$H]NLX was used to label MOR whilst [$^3$H]DPN was used to label both DOR and KOR. The potency of the new compounds in displacing the specific binding of the radioligand was determined by linear regression analysis of Hill plots. Specific (i.e., opioid receptor-related) binding at MOR, KOR and DOR was determined as the difference in binding obtained in the absence and presence of 5 μM naltrexone, U50,488 and SNC80, respectively. The $IC_{50}$ values were determined and converted to $K_i$ values using the Cheng—Prusoff equation (Rosenblum, A. et al. Exp Clin Psychopharmacol. 2008, 16 (5), 405-416).

[$^{35}$S]GTPγS Functional Assay

The [$^{35}$S]GTPγS functional assay was used to determine whether the synthesized compounds are agonists. The agonist's activity of the compounds was measured relative to 3 μM DAMGO at MOR. In this assay, upon receptor activation due to agonist binding, [$^{35}$S]GTPγS binds to the Gα subunit. Thus, [$^{35}$S]GTPγS replaces endogenous GTP and since the γ-thiophosphate bond is resistant to hydrolysis by GTPase, [$^{35}$S]GTPγS labelled Gα subunits accumulate and can be quantified by measuring the amount of incorporated [$^{35}$S].

Briefly, after thawing, membrane protein preparations were suspended in membrane (TME) buffer (50 mM Tris, 3 mM $MgCl_2$, 0.2 mM EGTA, and 100 mM NaCl adjusted to pH 7.7), homogenized, and centrifuged at 50000×g for 10 mins and then re-homogenized. The Bradford assay was then conducted to determine the concentration of the membrane protein using BSA as the standard. Suitable dilutions of membrane protein, [$^{35}$S]GTPγS), cold GTPγS, DAMGO and GDP were made in TME. The desired amount of the protein per tube was 10 μg. All the test-tubes were vortexed and incubated in the shaking water bath at 30° C. for 90 minutes, after which bound radioligand was filtered and rinsed three times with cold Tris buffer. The filtered bound radioligand was then transferred into scintillation tubes with 4 mL of scintillation fluid and radioligand was quantified. However, counting was delayed for 9 hrs to allow the radioactivity to enter the solution. Percent DAMGO stimulation was defined as (net stimulated binding of test compound/net stimulated binding of DAMGO)×100%. The normalized data were subjected to nonlinear regression analysis to determine $EC_{50}$ and $E_{max}$ values using Prism 6.0 software (GraphPad Software, San Diego, Calif.). The assay was performed in triplicate and repeated at least three times.

In Vivo Studies

For the in vivo studies, male Swiss Webster mice were used for both the warm-water immersion and opioid withdrawal assays. The mice weighed 23-35 g and were housed five to a cage in animal care quarters maintained at 22° C. on a 12 hour light-dark cycle with food and water available ad libitum. The mice were transferred to the test room and the tests were then conducted 18 hours later. Protocols and procedures were approved by the Institutional Animal Care and Use Committee at Virginia Commonwealth University Medical Center and complied with the recommendations of the International Association for the Study of Pain.

A 75 mg morphine pellet was implanted in to the base of the neck of the mice and the mice were then given time to recover in their home cages before the test was conducted. The mice were then allowed for 30 min habituation to an open-topped, square, clear Plexiglas observation chamber (26×26×26 cm$^3$) with lines partitioning the bottom into quadrants before they were given antagonist. All drugs and test compounds were administered subcutaneously (s.c.). Withdrawal was precipitated at 72 h from pellet implantation with naltrexone (1.0 mg/kg, s.c.), and the test compounds at indicated doses. Withdrawal commenced within 3 min after antagonist administration. Escape jumps, paw tremors and wet dog shakes were quantified by counting their occurrences over 20 min for each mouse using five mice per drug. The data is given as the mean±SEM. One-way ANOVA followed by the post hoc Dunnett test were performed to assess significance using the Prism 6.0 software.

Warm-Water Immersion Assay

Each indole analogue of naltrexamine was tested for its ability to produce antinociception and/or to antagonize the antinociceptive effects of morphine in mice using the warm-water tail immersion assay described by Coderre and Rollman. The a water bath temperature was maintained at 56±0.1° C. The baseline latency (control) was determined before injecting the compounds into the mice. The average baseline latency obtained for this experiment was 3.0±0.1 s and only mice with a baseline latency of 2 to 4 s were used. To test for agonism, the tail immersion was conducted 20 min (time that morphine effect starts to peak) after injecting the indole analogues of 6α/β-naltrexamine. To prevent tissue damage, a 10 s maximum cut off time was imposed. Antinociceptive response was calculated as the percentage maximum possible effect (% MPE), where % MPE=[(test−control)/(10−control)]×100. In the antagonism study, the 6α/β-naltrexamine derivatives were given 5 min before morphine. The tail immersion test was conducted 20 min after giving morphine. % MPE was calculated for each mouse using at least five mice per drug. AD$_{50}$ values were calculated using the least-squares linear regression analysis followed by calculation of 95% confidence interval by Bliss method. A higher % MPE indicates a stronger antinociception effect by the ligand.

Results

The Ki values obtained for the indole analogues of 6α-naltrexamine at MOR, KOR and DOR and the selectivity for MOR over KOR and DOR are shown in Table 2 whilst those for the indole analogues of 6β-naltrexamine are shown in Table 3.

TABLE 2

Binding affinity and selectivity of indole derivatives of 6α-naltrexamine

| Compd | R | K$_i$ (nM) ± SEM | | | Selectivity Ratio | |
|---|---|---|---|---|---|---|
| | | μ | κ | δ | κ/μ | δ/μ |
| NTX$^a$ | | 0.33 ± 0.02 | 1.44 ± 0.11 | 143.5 ± 13.7 | 4.4 | 435 |
| NAQ$^b$ | | 1.11 ± 0.07 | 13.3 ± 1.1 | 161.9 ± 15.0 | 12 | 146 |
| 1 | 2-indolyl | 0.363 ± 0.027 | 0.926 ± 0.125 | 14.244 ± 2.783 | 2.6 | 39.2 |
| 2 | 3-indolyl | 0.288 ± 0.042 | 0.984 ± 0.125 | 10.538 ± 2.888 | 3.4 | 37.0 |
| 3 | 4-indolyl | 0.264 ± 0.035 | 1.488 ± 0.349 | 9.260 ± 2.826 | 5.6 | 35.1 |

TABLE 2-continued

Binding affinity and selectivity of indole derivatives of 6α-naltrexamine

| Compd | R | K$_i$ (nM) ± SEM | | | Selectivity Ratio | |
|---|---|---|---|---|---|---|
| | | μ | κ | δ | κ/μ | δ/μ |
| 4 | (indol-5-yl) | 0.763 ± 0.112 | 3.447 ± 0.994 | 26.715 ± 7.722 | 4.5 | 35.0 |
| 5 | (indol-6-yl) | 0.434 ± 0.048 | 1.633 ± 0.277 | 12.775 ± 3.360 | 3.8 | 29.4 |
| 6 | (indol-7-yl) | 0.229 ± 0.015 | 1.693 ± 0.350 | 10.918 ± 2.938 | 7.4 | 47.7 |
| 7 | (indol-3-yl-methyl) | 0.837 ± 0.124 | 3.135 ± 0.449 | 9.169 ± 2.670 | 3.7 | 11.0 |
| 8 | (indol-3-yl-ethyl) | 0.437 ± 0.039 | 1.362 ± 0.178 | 31.231 ± 8.121 | 3.1 | 71.5 |

TABLE 2-continued

Binding affinity and selectivity of indole derivatives of 6α-naltrexamine

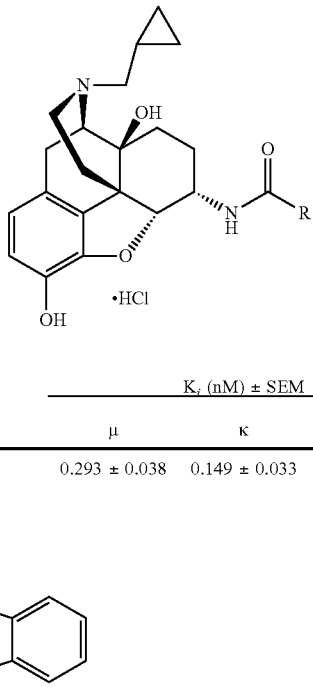

| Compd | R | $K_i$ (nM) ± SEM | | | Selectivity Ratio | |
| --- | --- | --- | --- | --- | --- | --- |
| | | μ | κ | δ | κ/μ | δ/μ |
| 9 | | 0.293 ± 0.038 | 0.149 ± 0.033 | 6.731 ± 0.396 | 0.5 | 23.0 |

[a]The Ki values of NTX and
[b]NAQ were obtained from previous experiments.

TABLE 3

Binding affinity and selectivity of indole derivatives of 6β-naltrexamine

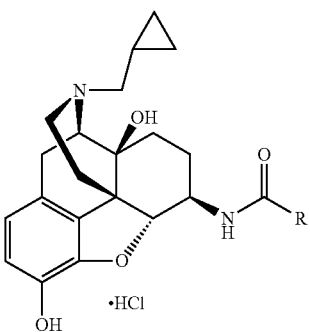

| Compd | R | $K_i$ (nM) ± SEM | | | Selectivity Ratio | |
| --- | --- | --- | --- | --- | --- | --- |
| | | μ | κ | δ | κ/μ | δ/μ |
| NTX[a] | | 0.33 ± 0.02 | 1.44 ± 0.11 | 143.5 ± 13.7 | 4.4 | 435 |
| NAQ[b] | | 1.11 ± 0.07 | 13.3 ± 1.1 | 161.9 ± 15.0 | 12 | 146 |
| 10 | | 0.287 ± 0.037 | 0.178 ± 0.002 | 1.544 ± 0.473 | 0.6 | 5.4 |

TABLE 3-continued

Binding affinity and selectivity of indole derivatives of 6β-naltrexamine

| Compd | R | $K_i$ (nM) ± SEM | | | Selectivity Ratio | |
|---|---|---|---|---|---|---|
| | | μ | κ | δ | κ/μ | δ/μ |
| 11 | (indol-3-yl) | 0.192 ± 0.016 | 0.160 ± 0.005 | 7.169 ± 1.232 | 0.83 | 37.3 |
| 12 | (indol-4-yl) | 0.235 ± 0.031 | 1.936 ± 0.299 | 45.878 ± 16.292 | 8.2 | 195.2 |
| 13 | (indol-5-yl) | 0.259 ± 0.037 | 0.512 ± 0.038 | 17.673 ± 4.780 | 2.0 | 68.2 |
| 14 | (indol-6-yl) | 0.250 ± 0.044 | 0.166 ± 0.012 | 6.231 ± 0.825 | 0.7 | 25 |
| 15 | (indol-7-yl) | 0.188 ± 0.011 | 0.520 ± 0.094 | 30.449 ± 9.494 | 2.8 | 162 |
| 16 | (indol-3-yl-methyl) | 0.241 ± 0.029 | 0.947 ± 0.114 | 37.019 ± 1.209 | 3.9 | 153.6 |

TABLE 3-continued

Binding affinity and selectivity of indole derivatives of 6β-naltrexamine

[Structure: 6β-naltrexamine core with NHC(=O)R substituent, ·HCl salt]

| Compd | R | $K_i$ (nM) ± SEM μ | $K_i$ (nM) ± SEM κ | $K_i$ (nM) ± SEM δ | Selectivity Ratio κ/μ | Selectivity Ratio δ/μ |
|---|---|---|---|---|---|---|
| 17 | [indol-3-yl-CH$_2$CH$_2$–] | 0.167 ± 0.012 | 0.387 ± 0.045 | 49.010 ± 4.717 | 2.3 | 293.5 |
| 18 | [indol-3-yl-CH$_2$CH$_2$CH$_2$–] | 0.203 ± 0.027 | 0.175 ± 0.037 | 25.299 ± 4.344 | 0.86 | 124.6 |

[a] The Ki values of NTX and
[b] NAQ were obtained from previous experiments.

MOR Binding for Indole Analogues of 6α-Naltrexamine

From the results obtained, it was observed that the position of the substitution on the indole ring did not affect the binding affinities significantly. Among the indole analogues of 6α-naltrexamine, compound 4 had the least binding affinity which was 3.3 fold worse than the compound 6 which had the best binding affinity at MOR. Also, increasing alkyl chain at position 3 did not affect binding affinity at MOR significantly. Compound 7 with the one carbon linker had the least binding affinity which was approximately 3 fold worse than compound 3 which has its carbonyl group directly attached to position 3 and compound 9 with the three carbon linker. The binding affinities of the compounds at MOR were similar to the binding affinities of NTX at MOR.

MOR Binding for Indole Analogues of 6β-Nahrexamine

The binding affinities at MOR for the indole analogues of 6β-naltrexamine were higher than their respective 6α-naltrexamine analogues. The Ki of all the indole analogues of 6β-naltrexamine at MOR was approximately 0.2 nM. Thus, neither the substitution position nor the length of the alky group at position 3 had any significant effect on binding affinity at MOR.

KOR Binding for Indole Analogues of 6α-Naltrexamine

The binding affinities for the indole analogues of 6α-naltrexamine was lower at KOR compared to MOR. Compound 4 with substitution at position 5 had the least binding to KOR. The binding affinities at KOR for the indole analogues of 6α-naltrexamine were similar to that of naltrexone at KOR. The position of substitution on the indole ring did not have a significant effect on the binding of the compounds at KOR. Also, increasing alkyl chain length at position 3 on the indole ring did not have any significant effect on KOR binding; however, compound 9 which had a three carbon linker had a greater binding affinity at KOR than MOR. Compound 9 was the only indole derivatives of 6α-naltrexamine that had a greater affinity at KOR than MOR.

KOR Binding for Indole Analogues of 6β-Naltrexamine

Again, the binding affinities at KOR for the indole analogues of 6β-naltrexamine were higher than their respective 6α-naltrexamine analogues. Among the indole analogues of 6β-naltrexamine, compound 12 (with substitution at position 4) had the least affinity for KOR. Also, increasing the alkyl chain at position 3 did not significantly alter the binding affinity. Most of the indole analogues of 6β-naltrexamine might either be dual MOR and KOR agonist or antagonists.

DOR Binding for Indole Analogues of 6α-Naltrexamine

The indole analogues of 6α-naltrexamine had the least binding affinities at DOR compared to MOR and KOR. Compound 8 with substitution at position 3 and a two carbon linker had the least binding to DOR. The position of substitution on the indole ring did not have a significant effect on the binding of the compounds at DOR. However, it was observed that the analogue that was substituted at position 4 (which had the best binding affinity compared to substitutions at other positions on the indole ring) had a binding affinity that was 3 fold better than compounds substituted at position 5 (which had the worst binding affinity compared to substitutions at other positions on the indole ring). Interestingly, it was observed that when the alkyl chain at position 3 was only a 1 carbon chain, there was little change in the binding affinity. However, upon increasing the chain length to 2 carbon atoms, the binding affinity decreased by three fold. On the other hand, when the chain length was increased to 3 carbon atoms, the binding affinity improved.

DOR Binding for Indole Analogues of 6β-Naltrexamine

Among the indole analogues of 6β-naltrexamine, compound 10 (with substitution at position 1) had the best binding affinity for DOR whilst compound 17 (with 2 carbon chain linker substituted at position 3) had the least binding affinity for DOR. It was also observed that, increasing the alkyl chain length at position 3 resulted in a reduction in DOR binding.

Selectivity for MOR Over KOR and DOR of Synthesized Compounds

Compound 6 and compound 12 had the best selectivity for MOR over KOR whilst compound 17 had the greatest selectivity for MOR over DOR. However, it's worth noting that among the 6α-naltrexamine analogues, compound 6 and compound 8 had good selectivity for MOR over DOR. Thus, compound 6 had a good selectivity when considering selectivity for MOR over both KOR and DOR.

Results of [$^{35}$S]GTPγS Functional Assay

The results from the [$^{35}$S]GTPγS functional assay are shown in Table 4 (indole analogues of 6α-naltrexamine) and Table 5 (indole analogues of 6β-naltrexamine). As can be seen, the position of substitution on the indole ring did not significantly affect potency and efficacy. All the compounds had partial agonist effect at MOR. Compound 6 (substitution at position 7) had the highest potency but the lowest efficacy at MOR. Compound 6 was more potent than NAQ but had similar efficacy as NAQ. Compound 1 had the highest efficacy at MOR. Increasing the alky chain at position 3 did not have a significant effect on potency and efficacy. Compound 9 with the three carbon linker was the most potent and efficacious.

Compounds 10, 11 and 14 were the most potent compounds and these compounds were the most efficacious having $E_{max}$ values greater than 70%. In fact, compound 10 with substitution at position 2 had the greatest efficacy among both the indole analogues of 6α and β naltrexamine, with an $E_{max}$ value of 92%. From the results obtained it was observed that substitution at position 2, 3 and 6 had a significant effect on potency and efficacy. It was also observed that increasing the alkyl chain length at position 3 did not significantly affect potency. However, as the alkyl chain increased, the efficacy decreased correspondingly.

TABLE 4

MOR [$^{35}$S]GTPγS binding functional assay results of indole derivatives of 6α-naltrexamine

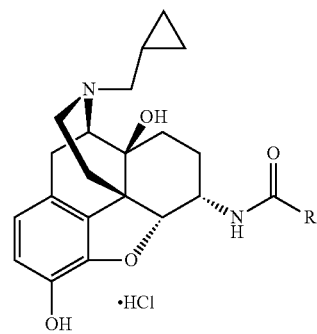

| Compound | R | $EC_{50}$(nM) ± SEM | $E_{max}$(% DAMGO) ± SEM |
|---|---|---|---|
| NTX[a] | | 0.16 ± 0.04 | 5.4 ± 0.8 |
| NAQ[a] | | 3.3 ± 0.4 | 20.8 ± 1.2 |
| 1 | indol-2-yl | 3.29 ± 1.32 | 52.0 ± 13.5 |
| 2 | indol-3-yl | 1.11 ± 0.09 | 35.4 ± 4.8 |
| 3 | indol-4-yl | 4.99 ± 2.19 | 28.9 ± 1 |
| 4 | indol-5-yl | 1.55 ± 0.08 | 32.2 ± 1.3 |
| 5 | indol-6-yl | 5.41 ± 1.52 | 27.0 ± 0.31 |
| 6 | indol-7-yl | 1.0 ± 0.1 | 20.95 ± 4.43 |
| 7 | (indol-3-yl)methyl | 4.92 ± 0.42 | 33.88 ± 1.43 |

TABLE 4-continued

MOR [$^{35}$S]GTPγS binding functional assay results of indole derivatives of 6α-naltrexamine

[Structure: 6α-naltrexamine core with NHC(=O)R substituent, ·HCl]

| Compound | R | EC$_{50}$(nM) ± SEM | E$_{max}$(% DAMGO) ± SEM |
|---|---|---|---|
| 8 | [indol-3-yl-ethyl] | 1.87 ± 0.42 | 41.10 ± 6.54 |
| 9 | [indol-3-yl-propyl] | 0.62 ± 0.13 | 48.36 ± 5.17 |

[a] The EC$_{50}$ and E$_{max}$ (% DAMGO) values of NTX and
[b] NAQ were obtained from previous experiments.

TABLE 5

MOR [$^{35}$S]GTPγS binding functional assay results of indole derivatives of 6β-naltrexamine

[Structure: 6β-naltrexamine core with NHC(=O)R substituent, ·HCl]

| Compound | R | EC$_{50}$(nM) ± SEM | E$_{max}$(% DAMGO) ± SEM |
|---|---|---|---|
| NTX[a] | | 0.16 ± 0.04 | 5.4 ± 0.8 |
| NAQ[a] | | 3.3 ± 0.4 | 20.8 ± 1.2 |
| 10 | 2-indolyl | 0.21 ± 0.01 | 92.4 ± 2.8 |
| 11 | 3-indolyl | 0.30 ± 0.03 | 70.45 ± 0.9 |
| 12 | 4-indolyl | 1.97 ± 0.12 | 15.21 ± 3.13 |
| 13 | 5-indolyl | 2.28 ± 0.19 | 20.15 ± 4.37 |
| 14 | 6-indolyl | 0.19 ± 0.02 | 71.8 ± 4.4 |
| 15 | 7-indolyl | 0.75 ± 0.20 | 32.0 ± 4.6 |

TABLE 5-continued

MOR [$^{35}$S]GTPγS binding functional assay results of indole derivatives of 6β-naltrexamine

[Structure: 6β-naltrexamine core with N-cyclopropylmethyl, OH groups, and NHC(O)R substituent at 6β position, ·HCl salt]

| Compound | R | EC$_{50}$(nM) ± SEM | E$_{max}$(% DAMGO) ± SEM |
|---|---|---|---|
| 16 | [CH$_2$-indol-3-yl] | 0.56 ± 0.18 | 50.17 ± 7.75 |
| 17 | [CH$_2$CH$_2$-indol-3-yl] | 0.39 ± 0.11 | 40.43 ± 5.28 |
| 18 | [CH$_2$CH$_2$CH$_2$-indol-3-yl] | 1.04 ± 0.17 | 36.29 ± 4.11 |

[a]The EC$_{50}$ and E$_{max}$ (% DAMGO) values of NTX and
[b]NAQ were obtained from previous experiments.

Results of Warm-Water Immersion Assay

Figure 1B:
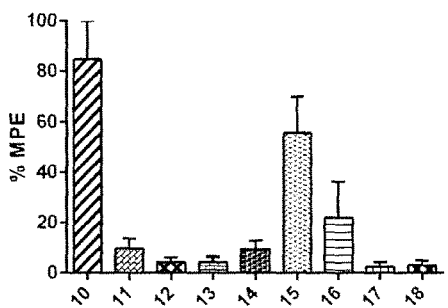
Figure 1C:
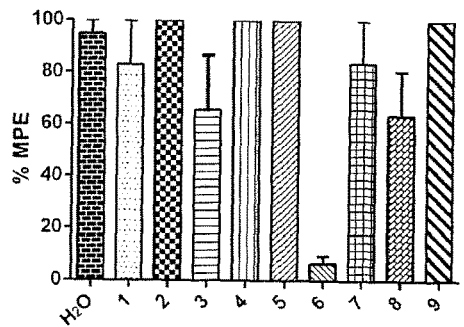
Figure 1D:
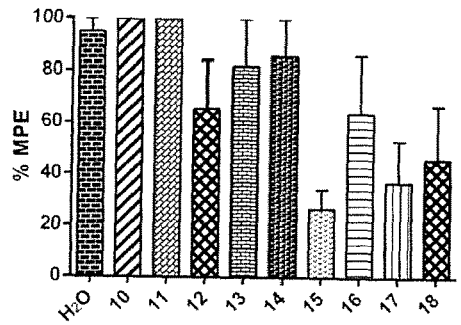
Figure 2A:
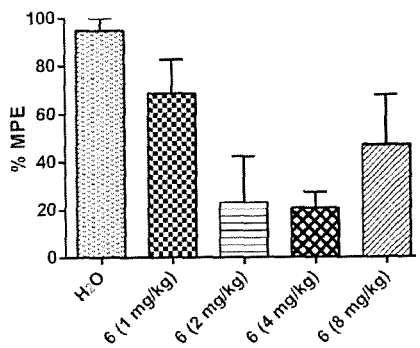
FIG. 2A-C. Dose dependent studies on compound 6 (A), 17 (B), and 18 (C) for opioid antagonist effect. Compounds 6, 17, and 18 had $AD_{50}$ values of 2.39 (0.46-12.47), 7.30 (3.38-15.74), and 9.64 (3.17-29.29) mg/kg (95% CL) respectively.
Figure 2B:
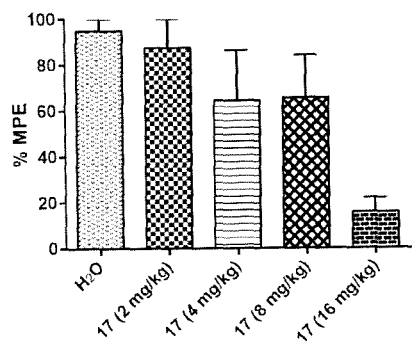
Figure 2C:
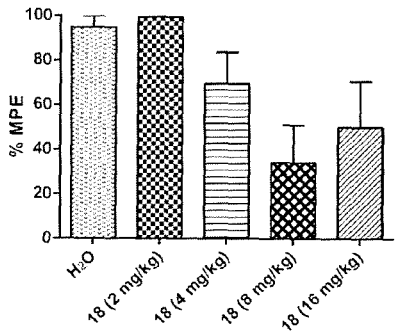

FIG. 1A shows the antinociceptive effects of the indole analogues of 6α-naltrexamine, while FIG. 1B shows the antinociceptive effects of the indole analogues of 6β-naltrexamine. Not surprisingly, compound 10, which was identified as a potent and efficacious MOR agonist, was also identified as an opioid agonist in the warm-water immersion assay. Compounds 15 and 16 were identified as partial opioid agonists. FIGS. 1C and D show the antinociceptive effect of morphine at 10 mg/kg in the presence of each indole analogue of 6α-naltrexamine (FIG. 1C) and 6β-naltrexamine (FIG. 1D) at 10 mg/kg. Compounds 6, 15, 17, and 18 effectively blocked morphine-mediated antinociception. Not surprisingly, compound 6, which had a high potency and the least efficacy in the [$^{35}$S]GTPγS functional assay, was identified as the most potent opioid antagonist in the warm-water immersion assay. The opioid antagonist effects of compound 6, 17, and 18 were dose dependent and their AD$_{50}$ values were 2.39 (0.46-12.47), 7.30 (3.38-15.74), and 9.64 (3.17-29.29) mg/kg (95% CL) respectively (FIG. 2A-C). The slight increase in the % MPE for compound 6 at 8 mg/kg in the dose response study could be due to the partial agonist effects of compound 6 or could be due to variability in the mice.

Results of Opioid Withdrawal Assay

Figure 3A:
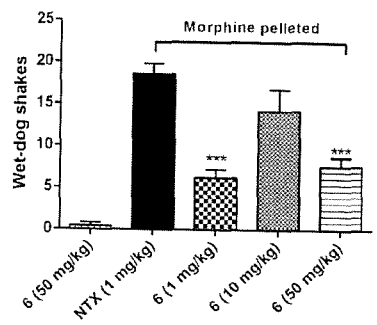
FIG. 3A-C. Compound 6 (s.c.) in opioid-withdrawal assays in chronic morphine-exposed mice (n=5): (A) Wet-dog shakes, (B) Escape jumps, and (C) Paw tremors. The first column in each figure represents placebo-pelleted mice while the second to the fourth represent morphine-pelleted mice. *** Indicates P<0.05, compared to 1 mg/kg naltrexone (NTX, s.c.), whilst * indicates P<0.1, compared to 1 mg/kg naltrexone (NTX, s.c.).
Figure 3B:
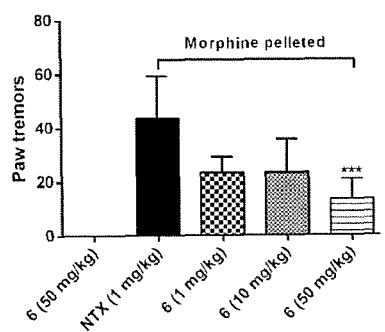
Figure 3C:
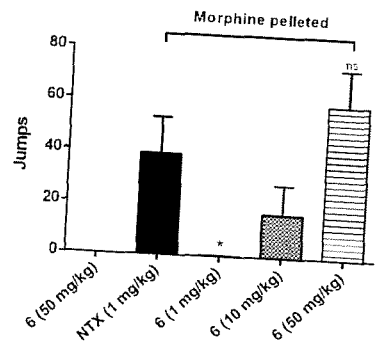

Compound 6 had the most promising pharmacological characteristics in the in vitro studies conducted compared to the other compounds synthesized. Compound 6 was also identified as the most potent opioid antagonist in the warm-water immersion assay. Therefore further in vivo studies were conducted on compound 6 using morphine-pelleted mice to determine if compound 6 had opioid withdrawal. The results showed that compound 6 itself did not induce any significant withdrawal symptoms in placebo-pelleted mice at 50 mg/kg (FIGS. 3A, B and C, first columns). On the other hand, a 1 mg/kg dose of naltrexone induced significant withdrawal signs immediately after injection in morphine-pelleted mice and gave 18.6±1.2 times wet-dog shakes, 43.4±15.7 paw tremors and 39.0±14.2 times escape jumps (FIGS. 3A, B and C, second columns). Secondly, compound 6 produced significantly less wet-dog shakes than naltrexone in morphine-pelleted mice even at dose of 50 mg/kg (FIG. 3A, column 4). Again, compound 6 produced significantly less paw tremors than naltrexone in morphine pelleted mice even at a high dose of 50 mg/kg (FIG. 3B, column 4). On the other hand, compound 6 at dose of 1 mg/kg produced significantly less escape jumps than naltrexone at a dose of 1 mg/kg in morphine pelleted mice (FIG. 3C, column 3). However, compound 6 produced more escape jumps at 50 mg/kg in morphine-pelleted mice than naltrexone at 1 mg/kg (FIG. 3C, column 5), but these results were not significantly different. Thus, compound 6 had less opioid withdrawal effects at a dose 26 times its AD$_{50}$ value and produced less significant withdrawal symptoms than naltrexone overall. It was also observed that both compound 6 and naltrexone at 1 mg/kg produced diarrhea in morphine pelleted mice but not in the placebo pelleted mice.

Example 2

Detailed Chemical Syntheses

Synthesis of 6α-Benzyl Naltrexamine

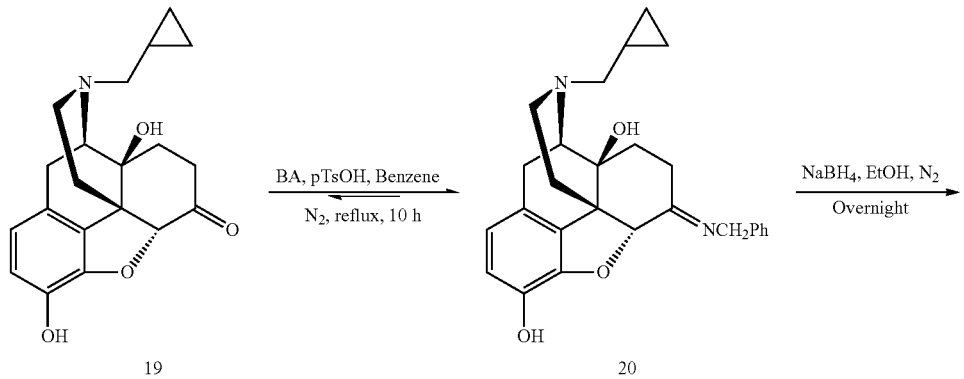

A benzene solution (150 mL) in a three-necked flask containing naltrexone base (19), benzyl amine (1.2 eq.) and a trace of p-toluene sulfonic acid was refluxed for 10 hours using a Dean-Stark trap for azeotropic removal of water. The mixture was then concentrated (30 mL) and $NaBH_4$, a-solute ethanol and 4 Å molecular sieves were added to the reaction mixture and stirred under $N_2$ overnight. When the reaction was completed, the solvent was removed using a rotavapor and the product purified using column chromatography with a Dichloromethane:Methanol:Ammonium hydroxide (40:1: 1%) mobile phase system to obtain 6α-benzyl naltrexamine (21) in 88% yield (Courtwright, D. T.; Joseph, H.; DesJarlais, D. Addicts Who Survived; University of Tennessee Press: Knoxville, Tenn., 1989).

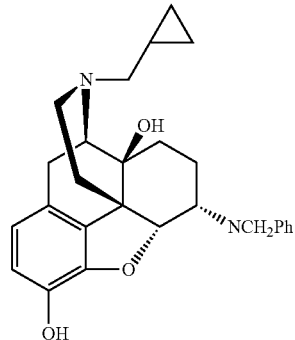

Synthesis of 6α-Naltrexamine HCl

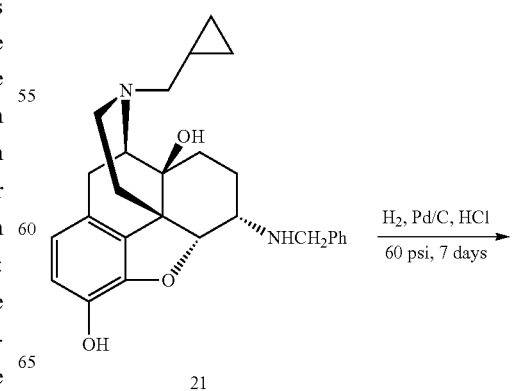

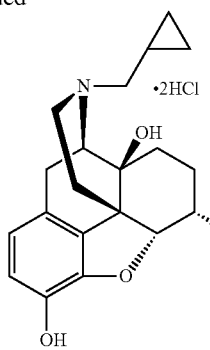

22

6α-benzyl naltrexamine (21) was dissolved in 35-60 mL of methanol and then concentrated HCl was added to obtain a pH of 2. 10% Pd/C (approximately 10% of the starting material) was added and hydrogenation was carried out at 60 psi for 6 days using a Parr hydrogenator. The Pd/C was changed every three days. When the reaction was completed, the Pd/C was filtered using celite to obtain pure 6α-naltrexamine HCL (22) with a yield of 76% (ibid).

Synthesis of 6β-Dibenzyl Naltrexamine

A toluene solution (150 mL) in a three-necked flask containing naltrexone base (19), benzoic acid (1.3 eq.), a trace of p-toluene sulfonic acid was stirred for 30 minutes at room temperature. Dibenzyl amine (1.3 eq.) was then added and the mixture refluxed with a Dean-Stark apparatus for 24 hours under $N_2$. The mixture was then concentrated to 30 mL, cooled and then 50 mL anhydrous ethanol and $NaCNBH_3$ (0.8 eq) were added and the reaction mixture was stirred under $N_2$ overnight. The mixture was then filtered with celite and the solvent was removed using a rotavapor apparatus. The solid obtained was refluxed with methanol for 1 hour and then cooled and filtered. The residue obtained was washed with cold methanol to obtain 6β-dibenzyl naltrexamine (24) in 71% yield (ibid).

Synthesis of 6β-naltrexamine HCl

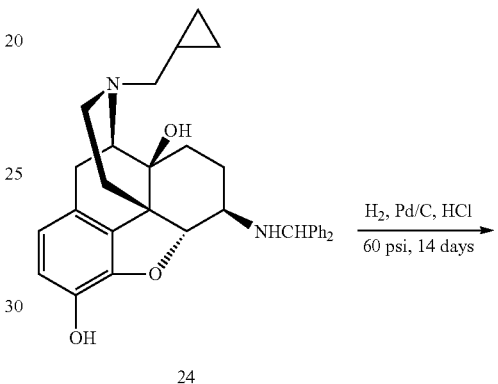

24

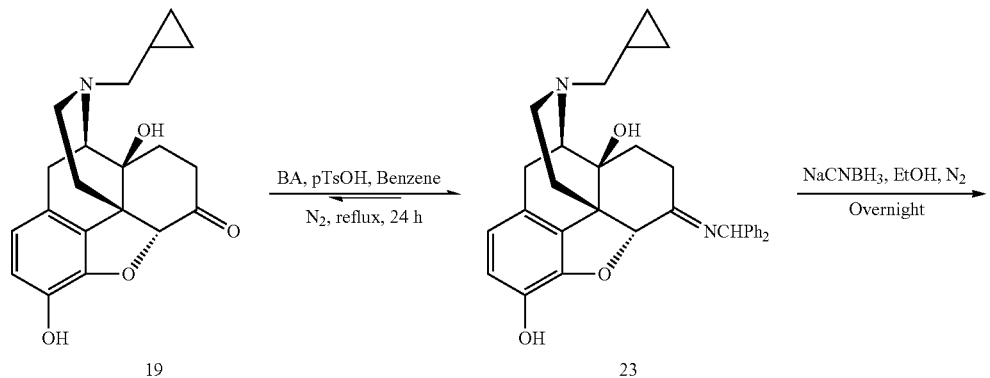

19            23

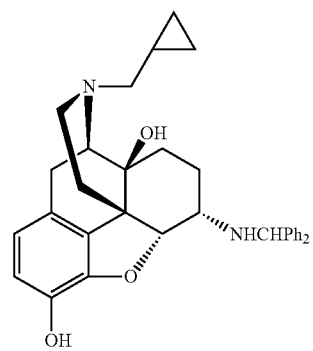

24

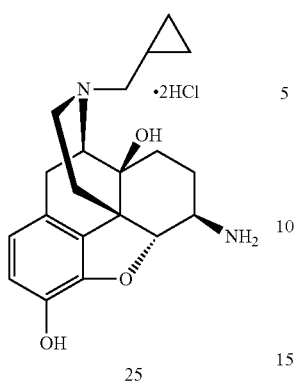

Dibenzyl naltrexamine (24) was dissolved in 35-60 mL of methanol and then concentrated HCL was added to obtain a pH of 2. 10% Pd/C (approximately 10% of the starting material) was added and hydrogenation was carried out at 60 psi for 6 days using a Parr hydrogenator. The Pd/C was changed every three days. When the reaction was completed, the Pd/C was filtered using celite to obtain pure 6β-naltrexamine HCl (25) with a yield of 82% (ibid).

General Method of Coupling of Naltrexamine to Carboxylic Acid Derivatives

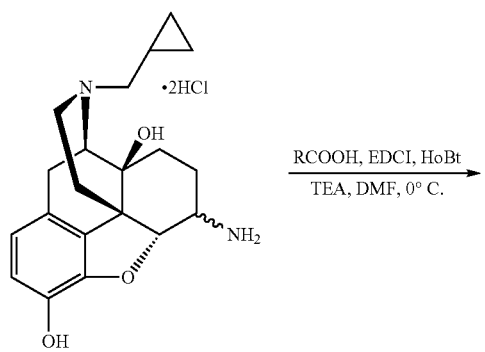

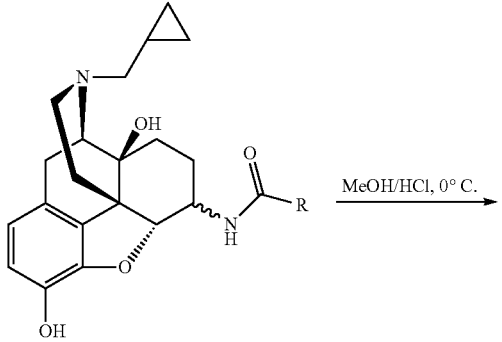

The carboxylic acid derivatives (3 eq.), hydrobenzotriazole (HoBt) (3eq.), 4 Å molecular sieves triethylamine (9 eq.), N-(3-Dimethylaminopropyl)-N'-ethylcarbodiimide hydrochloride (EDCI) (3 eq.), and DMF (2 mL) were added into a three-necked flask on an ice-water bath and stirred for 15 minutes. Naltrexamine (1 eq.) suspended in 2 mL DMF was added dropwise and then stirred on the water bath for 24 hours. When the reaction was completed, the reaction mixture was filtered with celite and the filtrate concentrated to remove DMF. MeOH (7 mL) and $K_2CO_3$ (3 eq.) were added to the concentrate and stirred at ambient temperature. When hydrolysis of the ester at position 3 was complete, the mixture was filtered through celite again and concentrated to remove MeOH. The mixture was then purified using column chromatography with dichloromethane:MeOH (20:1) and $NH_4OH$ to give the free base (Meldrum, M. L. A Capsule History of Pain Management. JAMA 2003, 290 (18), 2470-2475).

Characterization of Compounds

17-Cyclopropylmethyl-3,14β-dihydroxy-4,5α-epoxy-6α-(indole-2-carboxamido)morphinan (1)

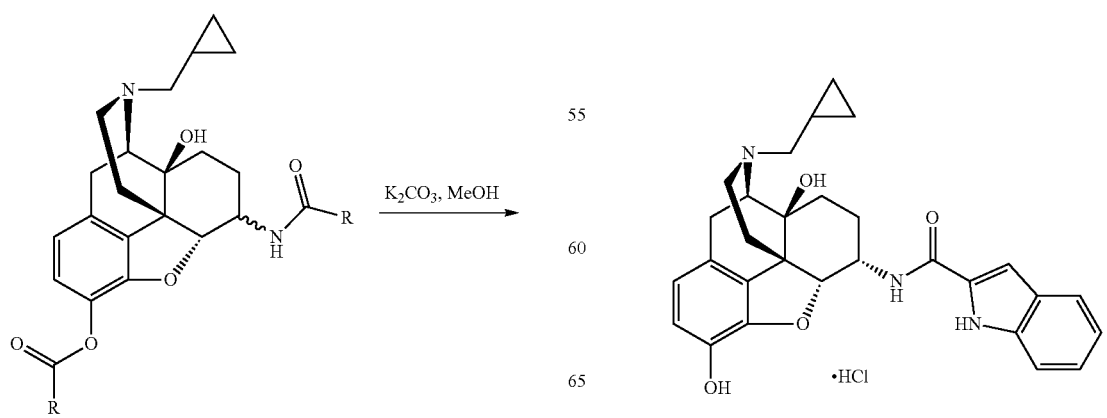

The title compound was prepared by following the general procedure in 81% yield. ¹HNMR (400 MHz, DMSO-d6) δ 11.65 (s, 1H, Exchangeable), 9.25 (s, 1H, Exchangeable), 8.87 (s, 1H, Exchangeable), 8.09 (d, J=7.76 Hz, 1H, Exchangeable), 7.62 (d, J=7.96 Hz, 1H), 7.45 (d, J=8.2 Hz, 1H), 7.23 (dd, J=7.96 Hz, 1.44 Hz, 1 H), 7.18 (d, J=8.2 Hz, 1H) 7.05 (t, J=7.88 Hz, 1H), 6.72 (d, J=8.08 Hz, 1H), 6.59 (d, J=8.16 Hz, 1H), 6.34 (s, 1H, Exchangeable), 4.79 (d, J=3.8 Hz, 1H) 4.62 (m, 1H), 3.93 (d, J=7 Hz, 1H), 3.40-3.26 (m, 2H), 3.12-3.05 (m, 2H), 2.96 (m, 1H), 2.73(m, 1H), 1.92 (m, 1H) 1.66 (d, J=10.56, 1H) 1.56-1.45 (m, 2H), 1.2 (m, 1H) 1.09 (m, 1H), 0.71-0.61 (m, 2H), 0.51-0.40 (m, 2H). ¹³C NMR (100 MHz, DMSO-d6) δ 160.45, 146.16, 138.79, 136.50, 131.46, 128.74, 126.95, 123.40, 122.16, 121.44, 119.73, 119.15, 118.55, 112.26, 103.77, 87.41, 69.41, 61.07, 59.70, 57.08, 45.57, 45.28, 30.23, 29.27, 23.57, 19.56, 5.70, 5.16, 2.60. HRMS m/z found 486.2414 [M+H]⁺. Calculated 485.2315. IR (ATR, cm⁻¹) $v_{max}$ 3146, 1633, 1544.97, 1505, 1457, 1341, 1312, 1235, 1173, 1116, 989, 810, 746.% Purity 97.69%.

17-Cyclopropylmethyl-3,14β-dihydroxy-4,5α-epoxy-6α-(indole-3-carboxamido)morphinan (2)

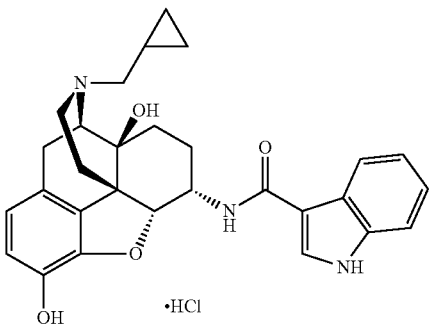

The title compound was prepared by following the general procedure in 29% yield. ¹HNMR (400 MHz, DMSO-d₆) δ 11.65 (s, 1H, exchangeable), 9.21 (s, 1H, exchangeable), 8.85 (s, 1H, exchangeable), 8.14(d, J=2.88, 1H, exchangeable), 8.11 (d, J=7.56, 1H), 7.45 (t, J=6.68, 2H), 7.18-7.09 (m, 2H), 6.71 (d, J=8.08, 1H), 6.58 (d, J=8.12, 1H), 6.27(s, 1H, exchangeable), 4.80(d,J=3.8, 1H), 4.66-4.60(m,1H), 3.91 (d, J=6.68, 1H), 3.12-3.05 (m, 2H), 2.95 (m, 1H), 2.74 (m, 1H), 1.90 (m, 1H), 1.66 (d, J=10.64, 1H), 1.56-1.44 (m, 2H), 1.11-1.06 (m, 2H), 0.71-0.61 (m, 2H), 0.51-0.40 (m, 2H). ¹³CNMR (100 MHz, DMSO-d₆) δ 164.32, 145.79, 138.41, 135.91, 128.82, 128.09, 125.73, 122.18, 122.07, 120.62, 119.31, 118.06, 111.90, 110.04, 87.85, 69.23, 60.97, 56.99, 45.13, 44.82, 30.12, 29.16, 23.36, 19.59, 5.55, 5.19, 2.41, 0.012. HRMS m/z found 486.2357 [M+H]⁺. Calculated 585.2315. IR (ATR, cm⁻¹) $v_{max}$ 3269, 1667, 1540, 1504, 1459, 1318, 1174, 1118.

17-Cyclopropylmethyl-3,14β-dihydroxy-4,5α-epoxy-6α-(indole-4-carboxamido)morphinan (3)

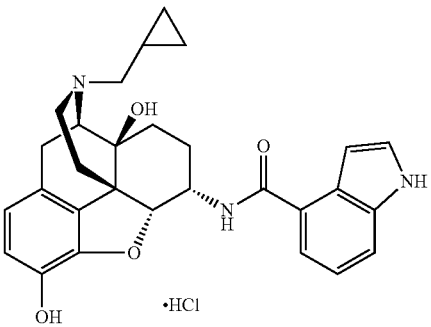

The title compound was prepared by following the general procedure in 81% yield. ¹HNMR (400 MHz, DMSO-d₆) δ 11.37 (s, 1H, exchangeable), 9.18 (s, 1H, exchangeable) 8.92 (s, 1H, exchangeable), 7.65 (d, J=8, 1H, exchangeable), 7.57 (d, J=8, 1H), 7.46-7.44 (m, 2H), 7.16 (t, J=7.72, 1H), 6.85 (s, 1H), 6.71 (d, J=8.04, 1H), 6.58 (d, J=8, 1H), 6.33 (s, 1H, exchangeable), 4.83 (d, J=3.24, 1H), 4.66 (m, 1H), 3.94 (d, J=6.08, 1H), 3.32 (s, 1H), 3.10 (m, 2H), 3.05 (m, 2H), 2.74 (m, 2H), 1.94 (m, 1H), 1.67 (d, J=12.92, 1H), 1.58 (m, 1H), 1.47 (m, 1H), 1.09 (m, 2H), 0.69 (m, 1H), 0.62 (m, 1H), 0.49 (m, 1H), 0.41 (m, 1H). ¹³CNMR (100 MHz, DMSO-d₆) δ 167, 145.62, 137.71, 136.30, 130.81, 126.53, 126.19, 125.36, 125.20, 120.34, 118.93, 118.77, 117.22, 114.36, 101.16, 88.85, 69.20, 61.27, 58.73, 54.59, 46.52, 45.99, 42.74, 29.27, 22.31, 20.32, 9.03, 3.80, 3.34. HRMS m/z found 486.2391 [M+H]⁺. Calculated 485.2315. IR (ATR, cm⁻¹) $v_{max}$ 3212, 2152, 1980, 1606, 1505, 1462, 1318, 1118, 771.% Purity 98.96%.

17-Cyclopropylmethyl-3,14β-dihydroxy-4,5α-epoxy-6α-(indole-5-carboxamido)morphinan (4)

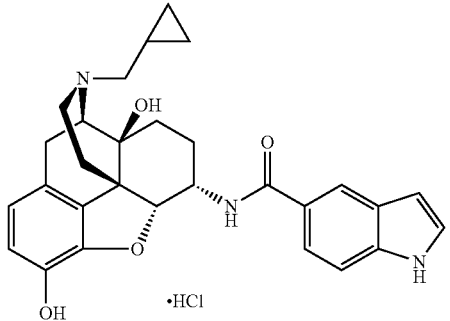

The title compound was prepared by following the general procedure in 85% yield. ¹HNMR (400 MHz, DMSO-d₆) δ 11.39 (s, 1H, exchangeable), 9.21 (s, 1H, exchangeable), 8.89 (s, 1H, exchangeable), 8.16 (S, 1H), 7.80 (d, J=7.76, 1H), 7.65 (d, J=8.44, 1H), 7.44 (d, J=8.84, 1H, exchangeable), 7.43 (s, 1H), 6.72 (d, J=8.04, 1H), 6.58 (d, J=8.08, 1H), 6.55 (s, 1H), 6.37 (s, 1H, exchangeable), 4.79 (d, J=3.52, 1H), 4.66-4.61 (m, 1H), 3.95 (d, J=6.24, 1H) 3.35 (s, 2H), 3.09-2.98 (m, 4H), 2.73 (m, 2H) 1.97-1.93 (m, 1H), 1.65 (d, J=12.04, 1H), 1.56-1.43 (m, 2H), 1.18-1.09 (m, 2H), 0.69-0.62 (m, 2H), 0.50 (m, 1H), 0.41 (m, 1H). ¹³CNMR (100 MHz, DMSO-d$_6$) δ 167.01, 146.10, 138.81, 137.43, 128.80, 126.92, 126.64, 125.33, 122.09, 120.66, 120.08, 119.06, 118.34, 110.85, 102.03, 87.55, 69.41, 61.02, 57.02, 45.79, 45.21, 39.54, 30.23, 29.29, 23.54, 19.61, 5.71, 5.17, 2.58. HRMS m/z found 486.2421 [M+H]$^+$. Calculated 485.2315. IR (ATR, cm$^{-1}$) ν$_{max}$ 3147, 1627, 1603, 1522, 1502, 1464, 1351, 1323, 1118, 1036, 771, 755, 726.% Purity 99.99%.

17-Cyclopropylmethyl-3,14β-dihydroxy-4,5α-epoxy-6α-(indole-6-carboxamido)morphinan (5)

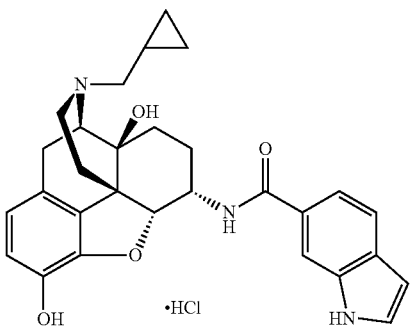

The title compound was prepared by following the general procedure in 75% yield. $^1$HNMR (400 MHz, DMSO-d$_6$) δ 11.43 (s, 1H, exchangeable), 9.21 (s, 1H, exchangeable) 8.88 (s, 1H, exchangeable), 7.98 (s, 1H), 7.85 (d, J=7.72, 1H, exchangeable), 7.61 (d, J=8.28, 1H), 7.54 (dd, J=1.32, 8.28, 1H), 7.50 (t, J=2.72, 1H), 6.73 (d, J=8.04, 1H), 6.58 (d, J=8.12, 1H) 6.49 (d, J=1.88, 1H), 6.35 (s, 1H, exchangeable), 4.81 (d, J=3.76, 1H), 4.63 (m, 1H), 3.94 (d, J=6.76, 1H), 3.3 (m, 2H), 3.11-3.05 (m, 2H), 2.98 (m, 1H), 2.72 (m, 1H), 1.94 (m, 1H), 1.65 (d, J=10.96, 1H), 1.57-1.43 (m, 2H), 1.23-1.09 (m, 3H), 0.71-0.59 (m, 2H), 0.50 (m, 1H), 0.40 (m, 1H). $^{13}$CNMR (100 MHz, DMSO-d$_6$) δ 167.16, 145.92, 138.53, 134.98, 129.89, 128.76, 127.88, 127.01, 122.15119.46, 119.24, 118.21, 118.10, 111.31, 101.26, 87.53, 69.29, 61.04, 57.03, 45.73, 45.17, 39.28, 30.17, 29.16, 23.44, 19.44, 5.60, 5.18, 2.49. HRMS m/z found 486.2371[M+H]$^+$. Calculated 485.2315. IR (ATR, cm$^{-1}$) ν$_{max}$ 3225, 2162, 1975, 1605, 1540, 1503, 1318, 1119, 1066, 780, 735.% purity 99.93.

17-Cyclopropylmethyl-3,14β-dihydroxy-4,5α-epoxy-6α-(indole-7-carboxamido)morphinan (6)

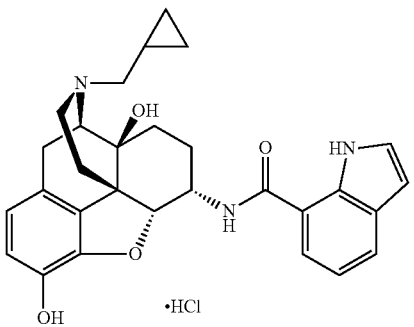

The title compound was prepared by following the general procedure in 22% yield. $^1$HNMR (400 MHz, DMSO-d$_6$) δ 11.13 (s, 1H, exchangeable), 9.25 (s, 1H, exchangeable), 8.91 (s, 1H, exchangeable), 8.14 (d, J=7.52, 1H, exchangeable), 7.74 (m, 2H), 7.36 (t, J=2.72, 1H), 7.09 (t, J=7.6, 1H), 6.71 (d, J=8.04, 1H), 6.58 (d, J=8.12, 1H), 6.50 (m, 1H), 6.39 (s, 1H, exchangeable), 4.88 (d, J=3.68, 1H), 14.70 (m, 1H), 3.95 (d, J=6.64, 1H), 3.12-3.04 (m, 3H), 2.94 (m, 1H), 2.73 (m, 2H), 2.00-1.92 (m, 1H), 1.68 (d, J=11.2, 1H), 1.56-1.45 (m, 3H), 1.24-1.18 (m, 1H), 1.08 (bs, 1H), 0.70 (m, 1H), 0.62 (m, 1H), 0.50 (m, 1H), 0.41 (m, 1H). $^{13}$CNMR (100 MHz, DMSO-d$_6$) δ 166.63, 145.93, 138.61, 133.95, 129.03, 128.69, 126.40, 123.86, 122.10, 120.24, 119.20, 118.17, 118.06, 116.80, 101.06, 87.30, 69.31, 69.01, 57.00, 45.61, 45.18, 30.22, 29.15, 23.45, 19.27, 5.62, 5.16, 2.53. HRMS m/z found 486.2408 [M+H]$^+$. Calculated 485.2315. IR (ATR, cm$^{-1}$) ν$_{max}$ 3060, 2166, 1634, 1585, 1504, 1456, 1312, 1280, 1123, 1030, 984.

17-Cyclopropylmethyl-3,14β-dihydroxy-4,5α-epoxy-6α-[2-(indol-3-yl)acetamido]morphinan (7)

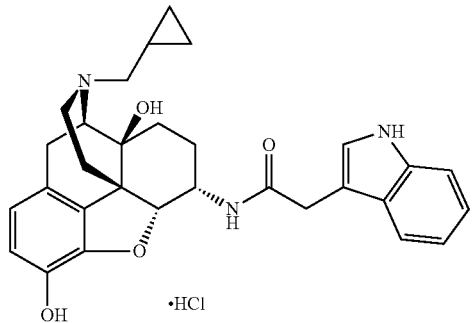

The title compound was prepared by following the general procedure in 80% yield. $^1$HNMR (400 MHz, DMSO-d6) δ 10.85 (s, 1H, exchangeable), 9.20 (s, 1H, exchangeable), 8.78 (s, 1H, exchangeable), 7.80 (d, J=7.96, 1H, exchangeable), 7.58 (d, J=7.92, 1H), 7.33 (d, J=8.08, 1H), 7.20 (d, J=2.28, 1H), 7.06 (t, J=7.50, 7.58, 1H), 6.96 (t, J=7.88, 7.04, 1H), 6.71 (d, J=8.08, 1H), 6.56 (d, J=8.16, 1H), 6.15 (s, 1H, exchangeable), 4.60 (d, J=3.88, 1H), 4.40 (m, 1H), 3.84 (d, J=6.84, 1H), 3.58 (s, 2H), 3.37(s, 2H), 3.07-3.00(m, 2H), 2.91 (m, 1H), 2.69 (m, 1H), 1.18 (m, 1H), 1.61 (d, J=10.76, 1H), 1.40 (q, J=10.52, 4.4, 9.92, 2H), 1.10 (m, 2H), 0.68 (m, 1H), 0.59 (m, 1H), 0.46 (m, 1H), 0.39 (m, 1H). $^{13}$CNMR (100 MHz, MeOD-d$_6$) δ 174.63, 185.37, 146.81, 139.41, 138.03, 131.58, 128.34, 126.14, 125.26, 122.75, 120.82, 120.16, 119.49, 118.91, 112.80, 109.25, 90.01, 71.39, 63.20, 60.22, 45.06, 37.47, 34.11, 33.81, 32.11, 29.98, 23.93, 21.85, 9.43, 5.13, 4.01. HRMS m/z found 500.2539 [M+H]$^+$. Calculated 499.25. IR (ATR, cm$^{-1}$) ν$_{max}$ 3218, 1640, 1506, 1317, 1234, 117, 1032, 746.% Purity 95.99%.

17-Cyclopropylmethyl-3,14β-dihydroxy-4,5α-epoxy-6α-[3-(indol-3-yl) propanamido)morphinan (8)

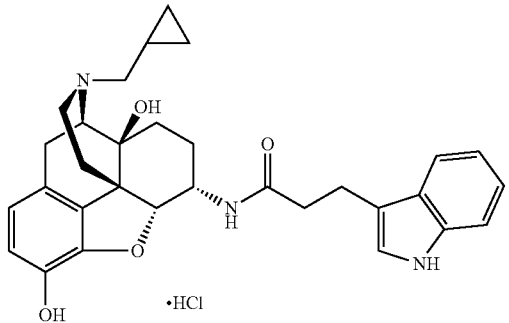

The title compound was prepared by following the general procedure in 55% yield. ¹HNMR (400 MHz, DMSO-d₆) δ 10.78 (s, 1H, exchangeable), 9.20 (s, 1H, exchangeable), 8.85 (s, 1H, exchangeable), 7.71 (d, J=8.08, 1H exchangeable), 7.53 (d, J=7.88, 1H), 7.32 (d, J=8.04, 1H), 7.12 (d, J=2.16, 1H), 7.05 (t, J=7.08, 1H), 6.97 (t, J=7.88, 1H), 6.71 (d, J=8.08, 1H), 6.55 (d, J=8.16, 1H), 6.28 (s, 1H, exchangeable), 4.57 (d, J=3.84, 1H), 4.42 (m, 1H), 3.90 (d, J=6.8, 1H), 3.25 (m, 1H), 3.17 (s, 2H), 3.07-3.01 (m, 2H), 2.93 (t, J=7.72, 3H), 2.74-2.66 (m, 1H), 2.53 (m, 1H), 2.44 (dd, 1=4.76, 13.36, 1H), 1.90-1.82 (m, 1H), 1.60 (d, J=10.92, 1H), 1.42-1.36 (m, 2H), 1.11-1.06 (m, 1H), 0.96-0.90 (m,1H), 0.70-0.59 (m, 2H), 0.50-0.46 (m, 1H), 0.42-0.37 (m, 1H). ¹³CNMR (100 MHz, DMSO-d₆) δ 169.37, 169.29, 143.31, 136.02, 133.54, 126.26, 124.50, 119.45, 118.46, 116.73, 115.85, 115.57, 111.26, 108.78, 85.09, 66.74, 58.46, 54.49, 45.97, 42.61, 42.29, 33.51, 27.59, 26.55, 20.90, 18.48, 17.08, 3.12, 2.70. HRMS m/z found 514.2691, [M+H]⁺. Calculated 513.2628. IR (ATR, cm⁻¹) $v_{max}$ 3267, 3146, 2157, 1670, 1616, 1543, 1504, 1463, 1427, 1343, 1316, 1172, 1118, 1031

17-Cyclopropylmethyl-3,14β-dihydroxy-4,5α-epoxy-6α-[4-(indol-3-yl) butanamido)morphinan (9)

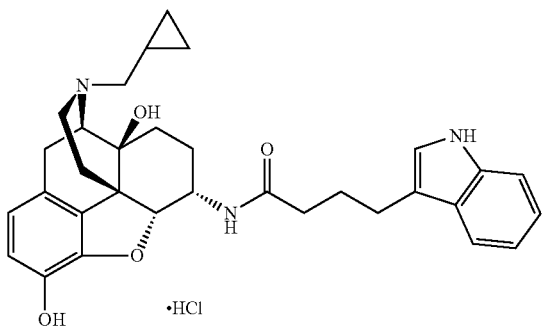

The title compound was prepared by following the general procedure in 34% yield. ¹HNMR (400 MHz, DMSO-d₆) δ 10.79 (s, 1H, exchangeable), 9.17 (s, 1H, exchangeable), 8.86 (s, 1H, exchangeable), 7.64 (d, J=8.04, 1H, exchangeable), 7.51 (d, J=7.84, 1H), 7.32 (d, J=8.04, 1H), 7.11 (d, J=2.16, 1H), 7.05 (t, J=7.04, 1H), 7.96 (t, J=7.88, 1H), 6.71 (d, J=8.08, 1H), 6.54 (d, J=8.12, 1H), 6.29 (s, 1H, exchangeable), 4.59 (d, J=3.88, 1H), 4.45-4.38 (m, 1H), 3.91 (d, J=6.8, 1H), 3.32 (d, J=19.72, 1H), 3.25 (m, 1H), 3.02 (m, 2H), 2.96 (m, 1H), 2.69 (t, J=7.4, 3H), 2.43 (dd, J=4.92, 13.32, 1H), 2.22 (t, J=7.32, 2H), 1.92-1.83 (m, 1H), 1.60 (d, J=13.16, 1H), 1.38 (m, 2H), 1.07 (m, 1H), 0.99-0.87 (m, 1H), 0.69-0.59 (m, 2H), 0.50-0.45 (m, 1H), 0.41-0.36 (m, 1H). ¹³CNMR (100 MHz, DMSO-d₆) δ 173.08, 146.69, 139.36, 137.00, 129.64, 127.98, 123.04, 122.95, 121.78, 120.15, 119.20, 119.07, 118.97, 115.05, 112.19, 88.45, 70.11, 61.85, 57.90, 45.98, 45.66, 35.98, 30.97, 29.95, 27.11, 25.11, 24.28, 20.41, 15.92, 6.46, 6.08, 3.34. HRMS m/z found 528.2876, 556.2742, 1055.5772 [M+H]⁺. Calculated 527.2784. IR (ATR, cm⁻¹) $v_{max}$ 3267, 3124, 2162, 1671, 1623, 1506, 1456, 1373, 1119

17-Cyclopropylmethyl-3,14β-dihydroxy-4,5α-epoxy-6β-(indole-2-carboxamido)morphinan (10)

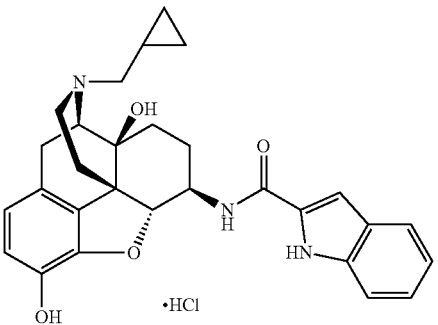

The title compound was prepared by following the general procedure in 32% yield. ¹HNMR (400 MHz, DMSO-d₆) δ 11.60 (s, 1H, exchangeable), 9.33 (s, 1H, exchangeable) 8.88 (s, 1H, exchangeable), 8.73 (d, J=7.92, 1H, exchangeable), 7.62 (d, J=7.96, 1H), 7.42 (d, J=8.24, 1H), 7.18 (m, 2H), 7.04 (t, J=7.52, 1H), 6.73 (d, J=8.08, 1H), 6.66 (d, J=7.96, 1H), 6.24 (s, 1H, exchangeable), 4.84 (d, J=7.72, 1H), 3.89 (s, 1H), 3.71 (m, 1H), 3.33 (m, 2H), 3.11-3.06 (m, 2H), 2.88 (m, 1H), 2.50 (m, 2H), 1.96-1.78 (m, 2H), 1.63 (m, 1H) 1.49-1.40 (m, 2H), 1.09 (s, 1H), 0.68 (s, 1H), 0.60 (s, 1H), 0.52 (s, 1H), 0.42 (s, 1H). ¹³CNMR (100 MHz, DMSO-d₆) δ 160.73, 142.02, 141.09, 136.23, 131.30, 129.62, 126.97, 125.26, 123.46, 121.52, 120.64, 119.83, 119.39, 117.87, 112.23, 102.63, 89.85, 69.62, 61.67, 56.69, 50.66, 46.37, 45.61, 29.37, 23.78, 22.91, 5.62, 5.07, 2.55. HRMS m/z found 486.2411 [M+H]⁺. Calculated 485.2315. IR (ATR, cm⁻¹) $v_{max}$ 3212, 2167, 1975, 1617, 1551, 1506, 1315, 1239, 1125, 1034, 815, 747, 668.% Purity 96.75%.

17-Cyclopropylmethyl-3,14β-dihydroxy-4,5α-epoxy-6β-(indole-3-carboxamido)morphinan (11)

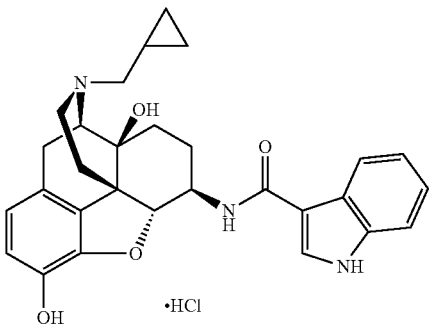

The title compound was prepared by following the general procedure in 27% yield. $^1$HNMR (400 MHz, DMSO-d$_6$) δ 11.64 (s, 1H, exchangeable), 9.34 (bs, 1H, exchangeable), 8.89 (s, 1H, exchangeable), 8.13-8.10 (m, 3H, 1 proton exchangeable), 7.42 (d, J=7.88, 1H), 7.16-7.06 (m, 2H), 6.73 (d, J=8.08, 1H), 6.65 (d, J=8.12, 1H), 6.24 (s, 1H, exchangeable), 4.82 (d, J=7.76, 1H), 3.90 (s, J=4.28, 1H), 3.70 (m,1H), 3.36 (s, 1H), 3.12-3.05 (m, 3H), 2.88 (m, 2H), 1.89 (q, J=12.32, 1H), 1.78 (d, J=13.2, 1H), 1.63 (m, 1H), 1.48-1.41 (m, 2H), 1.22 (bs, 1H), 0.68 (m, 1H), 0.50 (m, 1H), 0.52 (m, 1H), 0.42 (m, 1H). $^{13}$CNMR (100 MHz, DMSO-d$_6$) δ 164.46, 142.18, 141.03, 135.90, 129.70, 127.60, 125.86, 121.98, 120.89, 120.63, 120.43, 119.29, 117.89, 111.79, 110.30, 90.17, 69.69, 61.70, 56.70, 50.21, 46.38, 45.60, 29.40, 27.30, 23.99, 22.93, 5.61, 5.12, 2.53. HRMS m/z found 486.2411 [M+H]$^+$. Calculated 485.2315. IR (ATR, cm$^{-1}$) μ$_{max}$ 3267, 1671, 1621, 1539, 1505, 1455, 1313, 1176, 1119

17-Cyclopropylmethyl-3,14β-dihydroxy-4,5α-epoxy-6β-(indole-4-carboxamido)morphinan (12)

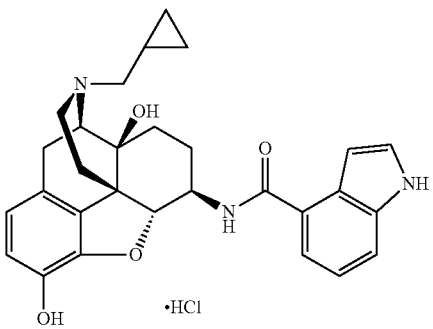

The title compound was prepared by following the general procedure in 31% yield. $^1$HNMR (400 MHz, DMSO-d$_6$) δ 11.31 (s, 1H, exchangeable), 9.34 (s, 1H, exchangeable), 8.87 (bs, 1H, exchangeable), 8.39 (d, J=8.12, 1H, exchangeable), 7.55 (d, J=8.04, 1H), 7.48 (d, J=7.16, 1H), 7.43 (m, 1H), 7.15 (t, J=7.72, 1H), 6.88 (s, 1H), 6.73 (d, J=8.12, 1H), 6.66 (d, J=8.16, 1H), 6.19 (s, 1H, exchangeable), 4.89 (d, J=7.76, 1H), 3.88 (d, J=4.92, 1H), 3.77-3.72 (m, 1H), 3.32 (m,1H), 3.13-3.04 (m, 2H), 2.87 (m,1H), 1.93 (q, J=12.08, 1H), 1.78 (d, J=13.68, 1H), 1.65 (m, 1H), 1.46 (m, 2H), 1.09 (t, J=6.96, 2H), 0.70-0.68 (m, 1H), 0.60 (m, 1H), 0.53-0.50 (m, 1H), 0.43-0.41 (m, 1H). $^{13}$CNMR (100 MHz, DMSO-d$_6$) δ 167.77, 142.15, 141.02, 136.35, 129.67, 126.30, 126.09, 125.75, 120.64, 120.19, 119.34, 118.50, 117.90, 114.31, 101.78, 89.92, 69.68, 61.68, 56.68, 50.89, 46.37, 45.61, 29.43, 27.29, 23.66, 22.90, 5.58, 5.11, 2.50. HRMS m/z found 486.2434 [M+H]$^+$. Calculated 485.2315. IR (ATR, cm$^{-1}$) μ$_{max}$ 3207, 2166, 1639, 1503, 1455, 1319, 1237, 1195, 1123, 1037, 917.

17-Cyclopropylmethyl-3,14β-dihydroxy-4,5α-epoxy-6β-(indole-5-carboxamido)morphinan (13)

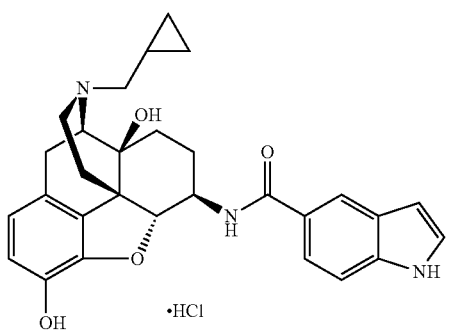

The title compound was prepared by following the general procedure in 61% yield. $^1$HNMR (400 MHz, DMSO-d$_6$) δ 11.36 (s, 1H, exchangeable), 9.32 (s, 1H, exchangeable) 8.88 (s, 1H, exchangeable), 8.48 (d, J=8.08, 1H, exchangeable), 8.18 (s, 1H), 7.66 (dd, J=1.56, 8.56, 1H), 7.42 (m, 2H), 6.73 (d, J=8.12, 1H), 6.65 (d, J=8.16, 1H), 6.53 (s, 1H), 6.20 (s, 1H, exchangeable), 4.89 (d, J=7.8, 1H), 3.88 (s, 1H), 3.71 (m, 1H), 3.35 (s, 2H), 3.11-3.04 (m, 2H), 2.87 (m, 1H), 1.90 (q, J=12.6, 1H), 1.78 (d, J=13.76, 1H), 1.62 (m, 1H), 1.49-1.39 (m, 2H), 1.09 (m, 1H), 0.68 (m, 1H), 0.59 (m, 1H), 0.52 (m, 1H), 0.42 (m, 1H). $^{13}$CNMR (100 MHz, DMSO-d$_6$) δ 166.77, 142.30, 141.30, 137.41, 129.77, 126.99, 126.60, 125.29, 120.56, 120.49, 119.91, 119.16, 117.92, 110.80, 102.05, 90.06, 69.80, 61.81, 56.74, 51.11, 46.52, 45.62, 29.44, 27.41, 23.93, 23.06, 5.72, 5.09, 2.65. HRMS m/z found 486.2434 [M+H]$^+$. Calculated 485.2315. IR (ATR, cm$^{-1}$) ν$_{max}$ 3125, 2162, 1980, 1622, 1595, 1547, 1360, 1311, 1249, 1124, 1037, 919, 760, 672.% Purity 98.51%.

17-Cyclopropylmethyl-3,14β-dihydroxy-4,5α-epoxy-6β-(indole-6-carboxamido)morphinan (14)

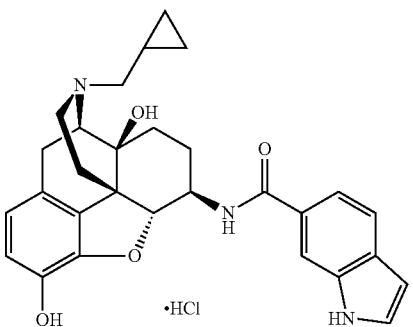

The title compound was prepared by following the general procedure in 29% yield. ¹HNMR (400 MHz, DMSO-d₆) δ 11.43 (s, 1H, exchangeable), 9.33 (s, 1H, exchangeable) 8.87 (s, 1H, exchangeable), 8.54(d, J=7.4, 1H, exchangeable), 7.99 (s, 1H), 7.58 (s, 2H), 7.50 (s, 1H), 6.73 (d, J=6.36, 1H), 6.66 (d, J=7.68, 1H), 6.49 (s, 1H), 6.20 (s, 1H, exchangeable), 4.90 (d, J=5.92, 1H), 3.88 (s, 1H), 3.71 (s, 1H), 3.17-3.06 (m, 2H), 2.89 (m, 2H), 2.5 (s, 1H), 1.90 (m, 1H), 1.78 (d, J=12.32, 1H), 1.62 (d, J=10.56, 1H), 1.49-1.39 (m, 2H), 1.09 (t, J=6.52, 2H), 0.68 (s, 1H), 0.60 (s, 1H), 0.52 (s, 1H), 0.42 (s, 1H). ¹³CNMR (100 MHz, DMSO-d₆) δ 166.85, 142.16, 140.23, 135.05, 129.76, 127.74, 127.20, 119.34, 118.39, 117.95, 116.98, 111.16, 101.20, 90.74, 69.62, 61.76, 58.35, 51.50, 49.99, 39.96, 39.76, 30.60, 29.99, 24.65, 22.25, 3.72, 3.46. HRMS m/z found 486.2396 [M+H]⁺. Calculated 485.2315. IR (ATR, cm⁻¹) $v_{max}$ 3223, 2152, 1970, 1608, 1551, 1312, 1035, 920, 820, 740.% Purity 99.86%.

17-Cyclopropylmethyl-3,14β-dihydroxy-4,5α-epoxy-6β-(indole-7-carboxamido)morphinan (15)

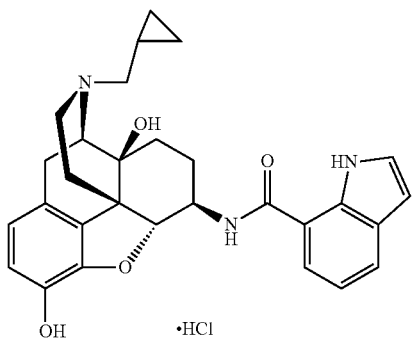

The title compound was prepared by following the general procedure in 56% yield. ¹HNMR (400 MHz, DMSO-d₆) δ 11.07 (s, 1H, exchangeable), 9.37 (s, 1H, exchangeable), 8.90 (s, 1H, exchangeable), 8.75 (d, J=8.04, 1H, exchangeable), 7.78-7.75 (dd, J=4.24, 3.12, 2H), 7.35 (t, J=2.6 1H), 7.10 (t, J=7.6, 1H), 6.74 (d, J=8.12, 1H), 6.67 (d, J=8.16, 1H), 6.49 (m, 1H), 6.26 (bs, 1H, exchangeable), 4.93 (d, J=7.8, 1H), 3.91 (d, J=4.84, 1H), 3.82-3.78 (m, 2H), 3.18-3.06 (m, 3H), 2.91-2.86 (m, 1H), 2.02-1.93 (q, J=11.56, 1H), 1.65 (m, 1H), 1.56-1.41 (m, 2H), 1.10 (t, J=7, 2H), 0.71-0.68 (m, 1H), 0.62-0.60 (m, 1H), 0.55-0.52 (m, 1H), 0.44-0.42 (m, 1H). ¹³CNMR (100 MHz, DMSO-d₆) δ 164.50, 139.51, 138.46, 131.48, 127.15, 126.67, 123.95, 121.72, 118.20, 117.28, 117.02, 115.79, 115.40, 113.77, 98.68, 87.35, 67.21, 62.45, 59.20, 54.25, 48.23, 43.86, 43.16, 26.96, 24.75, 21.14, 20.39, 12.43, 3.07, 2.65. HRMS m/z found 486.2411 [M+H]⁺. Calculated 485.2315. IR (ATR, cm⁻¹) $v_{max}$ 3090, 2162, 1979, 1633, 1540, 1327, 1248, 1040

17-Cyclopropylmethyl-3,14β-dihydroxy-4,5α-epoxy-6β-[2-(indol-3-yl)acetamido)morphinan (16)

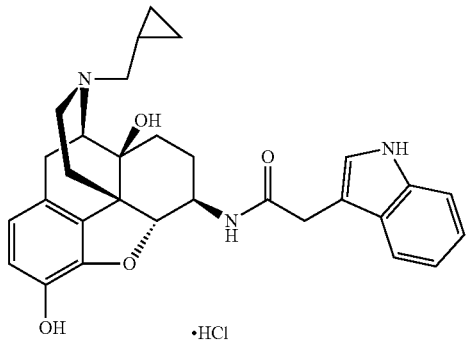

The title compound was prepared by following the general procedure in 49% yield. ¹HNMR (400 MHz, DMSO-d₆) δ 10.89 (s, 1H, exchangeable), 9.32 (s, 1H, exchangeable), 8.82 (s, 1H, exchangeable), 8.20 (d, J=7.92, 1H, exchangeable), 7.54 (d, J=7.76, 1H), 7.34 (d, J=8.04, 1H), 7.18 (d, J=2.08, 1H), 7.06 (t, J=7.08, 1H), 6.98 (t, J=7.24, 1H), 6.70 (d, J=8.12, 1H), 6.62 (d, J=8.16, 1H), 6.14 (s, 1H, exchangeable), 4.60 (d, J=7.84, 1H), 3.82 (d, J=5.2, 1H), 3.50 (q, J=14.96, 2H), 3.40 (m, 1H), 3.32 (m, 1H), 3.28 (s, 1H), 3.07-3.01 (dd, J=5.96, 19.24, 2H), 2.84 (m, 1H), 2.43-2.39 (m, 2H), 1.68 (m, 2H), 1.49-1.28 (m, 3H), 1.07 (m, 1H), 0.67-0.66 (m,1H), 0.60-0.56 (m, 1H), 0.51-0.48 (m, 1H), 0.41-0.39 (m, 1H). ¹³CNMR (100 MHz, DMSO-d₆) δ 170.94, 170.86, 141.99, 140.99, 135.88, 129.55, 127.03, 123.57, 121.02, 120.58, 119.36, 118.53, 118.42, 117.83, 111.28, 108.49, 99.49, 69.56, 61.54, 56.62, 46.32, 45.49, 32.78, 29.17, 27.21, 23.45, 22.82, 5.55, 5.08, 2.46. HRMS m/z found 500.2539 [M+H]⁺. Calculated 499.2471. IR (ATR, cm⁻¹) $v_{max}$ 3270, 1666, 1549, 1463, 1303, 1274, 1232, 1174, 1124, 1030, 898

17-Cyclopropylmethyl-3,14β-dihydroxy-4,5α-epoxy-6β-[3-(indol-3-yl) propanamido)morphinan (17)

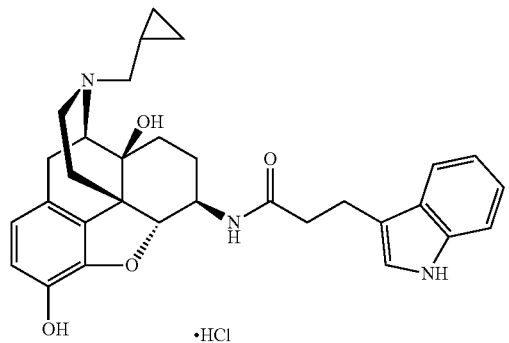

The title compound was prepared by following the general procedure in 70% yield. $^1$HNMR (400 MHz, DMSO-$d_6$) δ 10.77 (s, 1H, exchangeable), 9.34 (s, 1H, exchangeable), 8.83 (s, 1H, exchangeable), 8.14 (d, J=7.8, 1H, exchangeable), 7.52 (d, J=7.8, 1H), 7.32 (d, J=8.04, 1H), 7.10 (s, 1H), 7.06 (t, J=7.96, 1H), 6.97 (t, J=7.88, 1H), 6.72 (d, J=8.12, 1H), 6.63 (d, J=8.16, 1H), 6.18 (s, 1H, exchangeable), 4.55 (d, J=7.8, 1H), 3.85 (s, 1H), 3.45 (m, 1H), 3.34-3.29 (m, 2H), 3.09-3.00 (m, 2H), 2.92-2.83 (m, 3H), 2.45-2.42 (m, 4H), 1.71-1.68 (m, 2H), 1.53-1.50 (m, 1H), 1.42 (d, J=9.76, 1H), 1.33 (t, J=12.32, 1H), 1.08 (m, 1H), 0.68-0.63 (m, 1H), 0.60-0.57 (m, 1H), 0.52-0.48 (m, 1H), 0.42-0.38 (m, 1H). $^{13}$CNMR (100 MHz, DMSO-$d_6$) δ 141.98, 140.93, 135.97, 129.53, 126.86, 121.96, 120.98, 120.64, 119.41, 118.26, 117.89, 113.57, 111.27, 89.91, 69.58, 61.58, 56.67, 50.47, 46.31, 45.49, 39.62, 29.21, 27.21, 23.43, 22.83, 20.85, 5.55, 5.11, 2.47, 0.012. HRMS m/z found 514.2714, [M+H]$^+$. Calculated 513.2628. IR (ATR, cm$^{-1}$) $v_{max}$ 3187, 2160, 1640, 1541, 1505, 1450, 1325, 1271, 1234, 1124, 1032, 854

17-Cyclopropylmethyl-3,14β-dihydroxy-4,5α-epoxy-6β-[4-(indol-3-yl) butanamido)morphinan (18)

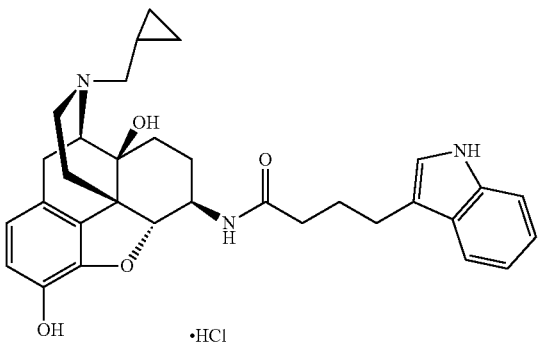

The title compound was prepared by following the general procedure in 39% yield. $^1$HNMR (400 MHz, DMSO-$d_6$) δ 10.79 (s, 1H, exchangeable), 9.35 (bs, 1H, exchangeable), 8.84 (s, 1H, exchangeable), 8.09 (d, J=7.88 1H, exchangeable), 7.51 (d, J=7.84, 1H), 7.33 (d, J=8.04, 1H), 7.12 (d, J=2.08, 1H), 7.08 (t, J=7.46, 1H), 6.97 (t, J=7.42, 1H), 6.72 (d, J=8.12, 1H), 6.64 (d, J=8.16, 1H), 6.18 (bs, J=1H, exchangeable), 4.56 (d, J=7.84, 1H), 3.85 (d, J=4.84, 1H), 3.09-3.03 (dd, J=5.88, 19.48, 2H), 2.88-2.84 (m, 1H), 2.68 (t, J=7.48, 2H), 2.44-2.41 (m, 2H), 2.16 (t, J=7.32, 2H), 1.89-1.85 (m, 2H), 1.75-1.70 (m, 2H), 1.56-1.53 (m, 1H), 1.43 (d, J=9.68, 1H), 1.38-1.31 (m, 1H), 1.12-1.05 (m, 2H), 0.69-0.67 (m, 1H), 0.61-0.58 (m, 1H), 0.53-0.50 (m, 1H), 0.43-0.40 (m, 1H). $^{13}$CNMR (100 MHz, DMSO-$d_6$) δ 142.02, 140.99, 136.07, 129.56, 127.05, 122.03, 120.88, 120.60, 119.35, 118.28, 118.18, 117.87, 114.11, 111.27, 89.88, 69.59, 67.88, 61.59, 56.65, 50.44, 46.33, 45.49, 29.24, 27.22, 26.15, 24.05, 23.53, 22.85, 15.00, 5.56, 5.10, 2.48. HRMS m/z found 528.2874 [M+H]$^+$. Calculated 527.2784. IR (ATR, cm$^{-1}$) $v_{max}$ 3268, 1671, 1633, 1505, 1455, 1423, 1316, 1178, 1127, 1033

17-Cyclopropylmethyl-3,14β-Dihydroxy-4,5α-Epoxy-6α-(Isoquinoline-3-Carboxamido)morphinan (NAQ)

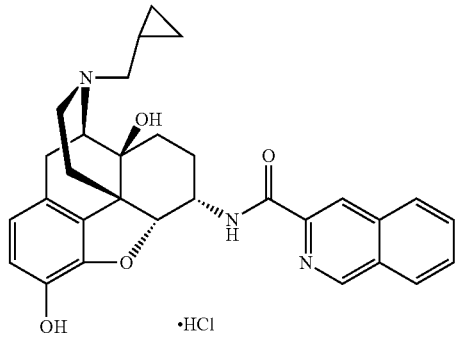

$^1$HNMR (400 MHz, DMSO-$d_6$) δ 9.44 (s, 1H), 8.98 (bs, 1H, exchangeable), 8.65 (s, 1H), 8.57 (d, J=8.76, exchangeable), 8.28 (d, J=8.08, 1H), 8.24 (d, J=8.08, 1H), 7.94 (t, J=8.04, 1H), 7.85 (d, J=8, 1H), 6.80 (d, J=8.04, 1H), 6.60 (d, J=8.16, 1H), 4.80 (d, J=3.76, 1H), 4.77-4.70 (m, 1H), 4.03 (d, J=6.68, 1H), 3.38 (d, J=19.68, 1H), 3.31-3.25 (m, 1H), 3.13-3.02 (m, 3H), 2.78-2.72 (m, 1H), 2.57 (dd, J=4.76, 13.6, 1H), 2.04-1.98 (m, 1H), 1.68-1.65 (m, 2H), 1.50-1.44 (m, 1H), 1.14-1.02 (m, 2H), 0.72-0.66 (m, 1H), 0.65-0.62 (m, 1H), 0.53-0.50 (m, 1H), 0.43-0.41 (m, 1H). $^{13}$CNMR (100 MHz, DMSO-$d_6$) δ 163.46, 151.54, 145.32, 141.94, 138.54, 135.30, 132.08, 129.72, 129.12, 128.66, 128.07, 127.91, 122.03, 120.21, 119.73, 118.12, 87.44, 69.21, 57.05, 48.43, 45.27, 45.17, 45.07, 29.92, 28.87, 23.31, 19.82, 5.50, 5.19, 2.38. HRMS m/z found 498.2461 [M+H]$^+$. Calculated 497.2315. IR (ATR, cm$^{-1}$) $v_{max}$ Instruments Used for Characterization The Bruker 400 MHz NMR was used to determine the $^1$H and $^{13}$C NMR spectra of the compounds. The masspec and IR spectra were determined using the Perkin Elmer ToF mass spectrometer and Thermo Scientific smart iTR instruments respectively. The purity of the compounds was determined using Varian Prostar HPLC instrument. The HPLC parameters used were: column=C18, injection volume=5 μL, sample concentration=3 mM, mobile phase=60 H2O:40 MeCN, flowrate=1 mL/min, detector=UV detection at 210 and 254 nm.

Example 3

Molecular Modeling Studies

Molecular modeling studies were conducted to observe the binding interactions of compound 6 with MOR. Chemical structures of the compounds were sketched in SybylX-2.1, and Gasteiger-Hückel charges were assigned before energy minimization (100 000 iterations) with the Tripos Force Fields. The X-ray crystal structure for MOR (4DKL) was retrieved from the Protein Data Bank (PDB) and prepared for docking by adding hydrogens and deleting water molecules and bound ligands inside the binding pocket.

Molecular Docking Study

Automated docking on MOR was done utilizing genetic algorithm docking program GOLD 5.4. The binding site was defined to include all atoms within 10 Å of the γ-carbon atom of Asp147 along with a hydrogen bond constraint between the 17-N of the ligand's morphinan skeleton and the carboxylate group of Asp147. Pictures were generated using PyMOL Molecular Graphics System, version 1.7.4.5

Compound 6 was first sketched with sybylx2.1 and then docked 50 times into the crystal structure of MOR (4dkl). From the docking results obtained, it was observed that compound 6 docked in two sites (not shown). The morphinan part of the compound was docked in the same position in both sites, however, the indole ring was docked differently. In binding site 1, the nitrogen of the indole ring was hydrogen bonded to K303 and the indole ring formed pi-pi interactions with W318. In binding site 2, the nitrogen of the indole ring formed hydrogen bonds with K233. The orientation of the indole ring was away from W318 and pi-pi stacking was not observed. The CHEM-PLP scores for the two binding sites were quite similar, however binding pose 1 had better GOLD and HINT scores than binding pose 2 (not shown).

Molecular Dynamics Simulation

The best CHEM-PLP-scored solutions for binding pose 1 and 2 were chosen for molecular dynamics (MD) studies. Force field parameter and topology files for NNQ were generated utilizing CGenFF. Coordinates for the spatial arrangement of the receptors within the lipid bilayer were retrieved from the Orientations of Proteins in Membranes (OPM) database. The simulation system, consisting of the receptor—ligand complex embedded in a lipid (POPC) bilayer surrounded with saline solution (0.15 MNaCl) was created in VMD 1.9.3 using the CHARMM force field topology file. All simulations were performed under hybrid CHARMM force field parameters that included protein, lipids and ligand with a time-step of 2 femtoseconds (fs). Periodic boundary conditions were employed, and Particle Mesh Ewald (PME) summation was used to calculate long-range electrostatic interactions. Non-bonded interactions were calculated with a smooth cutoff at 14 Å with a frequency of 2 fs. The temperature was maintained at 310 K via Langevin dynamics. All molecular modeling simulations were performed using NAMD 2.8. MD simulations were carried out in four stages. In the first stage, equilibration of the fluid-like lipid bilayer was performed via minimization (1000 iterations) followed by NPT equilibration (pressure equilibration, 0.5 ns) of the lipid tails only. In the second stage, an NPT equilibration of the system was run for a period of 1 ns with harmonic constraints placed on protein and NNQ atoms (5 kcal/(mol·Å)). The harmonic restraint was released in stage 3 and the entire system was equilibrated using the NVT canonical ensemble for a further 1 ns. The final production run was conducted for 10 ns using an NVT ensemble. Energy landscape analysis was performed using the NAMD Energy 1.4 plug-in; non-bonded interaction analyses were performed at various distances with a dielectric constant of 6.5. The best-scored poses based on the NAMD non-bonded interactions were selected for further analysis.

For binding pose 1, it was observed that after 1 ns of simulation, the indole ring of compound 6 still formed pi-pi interactions with W318. The nitrogen of the indole ring was hydrogen bonded to K303. However, it was observed that after 10 ns of simulation the indole ring moved into the binding pocket 2. In the case of binding pose 2), it was observed that there was no change in the binding pose after 1 ns of MD simulation nor after 10 ns. It was observed that the RMSD for binding pose 2 was lower than that of binding pose 1 during the simulation. The HINT score fore binding pose 2 improved after 10 ns of simulation but that of binding pose 1 worsened. Thus, compound 6 binds to MOR by interacting with K233, D147, Y148, and Y326 (binding pose 2).

SUMMARY

These Examples describe new morphinan analogues which are highly selective and reversible MOR antagonists. The MOR binding affinities of several compounds in this series were determined and the results showed that all compounds tested bound with high affinity (≤5 nM). In fact, several bound with sub-nM affinity (in the range of 100-500 pM). These results indicate that the molecular design strategy was successful in producing very high affinity MOR ligands.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound with generic Formula I:

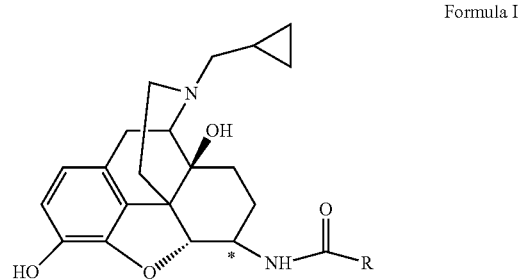

Formula I and salts thereof, wherein * indicates a chiral C that can be either an R configuration or an S configuration in terms of chirality and n is a range of 0 to 3;

and R of Formula I is selected from the group consisting of:

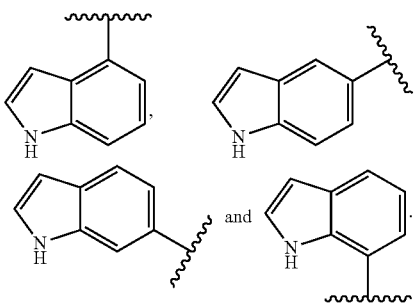

2. A method of treating opioid addiction in a subject in need thereof, comprising administering to the subject a therapeutically effective amount of a compound of Formula I:

Formula I

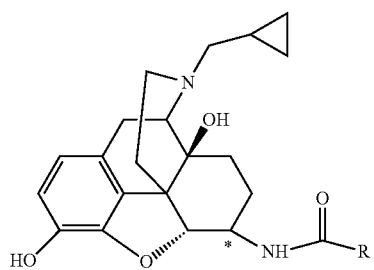

or a physiologically acceptable salt thereof,
wherein * indicates a chiral C that can be either an R configuration or an S configuration in terms of chirality and n is a range of 0 to 3;
and R of Formula I is selected from the group consisting of:

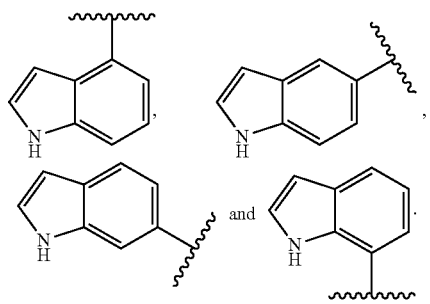

3. A method of treating pain in a subject in need thereof, comprising
administering to the subject a therapeutically effective amount of a compound of Formula I:

Formula I

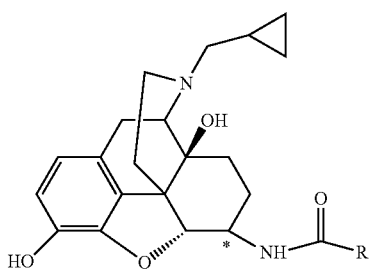

or a physiologically acceptable salt thereof,
wherein * indicates a chiral C that can be either an R configuration or an S configuration in terms of chirality and n is a range of 0 to 3;
and R of Formula I is selected from the group consisting of:

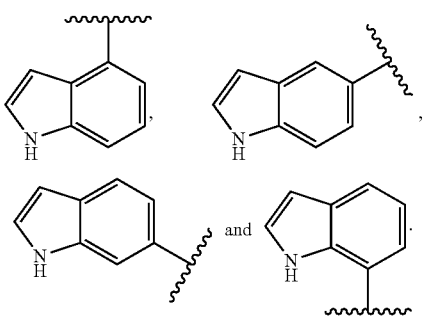

* * * * *